United States Patent
Corthésy et al.

(10) Patent No.: US 10,829,542 B2
(45) Date of Patent: Nov. 10, 2020

(54) METHODS FOR AFFECTING *SALMONELLA* INFECTIONS

(71) Applicants: CSL BEHRING AG, Bern (CH); CENTRE HOSPITALIER UNIVERSITAIRE VAUDOIS, Lausanne (CH)

(72) Inventors: Blaise Corthésy, Thierrens (CH); Gilles Bioley, Fiez (CH); Cédric Pierre Vonarburg, Bern (CH)

(73) Assignees: CSL BEHRING AG, Bern (CH); CENTRE HOSPITALIER UNIVERSITAIRE VAUDOIS, Lausanne (CH)

( * ) Notice: Subject to any disclaimer, the term of this patent is extended or adjusted under 35 U.S.C. 154(b) by 0 days.

(21) Appl. No.: 16/470,663

(22) PCT Filed: Dec. 20, 2017

(86) PCT No.: PCT/EP2017/083693
§ 371 (c)(1),
(2) Date: Jun. 18, 2019

(87) PCT Pub. No.: WO2018/115048
PCT Pub. Date: Jun. 28, 2018

(65) Prior Publication Data
US 2019/0345229 A1 Nov. 14, 2019

(30) Foreign Application Priority Data
Dec. 20, 2016 (EP) .................... 16205456

(51) Int. Cl.
*A61K 39/00* (2006.01)
*A61K 39/02* (2006.01)
*A61K 39/395* (2006.01)
*C07K 16/06* (2006.01)

(52) U.S. Cl.
CPC .......... *C07K 16/06* (2013.01); *C07K 2317/30* (2013.01)

(58) Field of Classification Search
CPC ....... A61K 39/00; A61K 39/02; A61K 39/395
USPC ...... 424/9.1, 9.2, 130.1, 163.1, 234.1, 258.1
See application file for complete search history.

(56) References Cited

FOREIGN PATENT DOCUMENTS

WO WO 2013/132052 A1 9/2013
WO WO 2013/132053 A1 9/2013

OTHER PUBLICATIONS

Longet., S, et al. Journal of Biological Chemistry, vol. 288, No. 6, pp. 4085-4094, Feb. 2013.*
International Prelimanary Report on Patentability and Written Opinion of the International Searching Authority, dated Jul. 4, 2019, for International Application No. PCT/EP2017/083693.
Acred et al., "Guidelines for the welfare of animals in rodent protection tests", Laboratory Animals, vol. 28, 1994, pp. 13-18.
Brandtzaeg, "Mucosal Immunity: Induction, Dissemination, and Effector Functions", Scandinavian Journal of Immunology, vol. 70, 2009, pp. 505-515.
Chairatana et al., "Defensins, lectins, mucins, and secretory immunoglobulin A: microbe-binding biomolecules that contribute to mucosal immunity in the human gut", Critical Reviews in Biochemistry and Molecular Biology, vol. 52, No. 1, 2017 (Published online Nov. 13, 2016), pp. 45-56 (13 pages).
Corthésy et al., "Secretory Immunoglobulin A: from Mucosal Protection to Vaccine Development", Biol. Chem., vol. 380, Nov. 1999, pp. 1251-1262, XP009107514.
Corthésy, "Role of secretory IgA in infection and maintenance of homeostasis", Autoimmunity Reviews, vol. 12, 2013 (Available online Nov. 29, 2012), pp. 661-665.
Cramer et al., "Stability over 36 months of a new liquid 10% polyclonal immunoglobulin product (IgPro 10, Privigen©) stabilized with L-proline", Vox Sanguinis, vol. 96, 2009 (published online Jan. 7, 2009), pp. 219-225.
Crottet et al., "Secretory Component Delays the Conversion of Secretory IgA into Antigen-Binding Competent F(ab')2: A Possible Implication for Mucosal Defense", J. Immunol, vol. 161, 1998, pp. 5445-5453 (10 pages total).
Dolowschiak et al., "IFN-γ Hinders Recovery from Mucosal Inflammation during Antibiotic Therapy for *Salmonella* Gut Infection", Cell Host & Microbe, vol. 20, Aug. 10, 2016, pp. 238-249 (13 toatal pages).
Hoiseth et al., "Aromatic-dependent *Salmonella typhimurium* are non-virulent and effective as live vaccines", Nature, vol. 291, May 21, 1981, pp. 238-239.
Kadaoui et al., "Secretory IgA Mediates Bacterial Translocation to Dendritic Cells in Mouse Peyer's Patches with Restriction to Mucosal Compartment", J. Immunol, vol. 179, 2007, pp. 7751-7757 (8 pages total).
Levinson et al., "Rapid Effects of a Protective O-Polysaccharide-Specific Monoclonal IgA on Vibrio cholerae Agglutination, Motility, and Surface Morphology", Infection and Immunity, vol. 83, No. 4, Apr. 2015, pp. 1674-1683.
Liang et al., "Identification of Chromosomal Errors in Human Preimplantation Embryos with Oligonucleotide DNA Microarray", PLOS ONE, vol. 8, Issue 4, e61838, Apr. 2013, pp. 1-11.

(Continued)

Primary Examiner — Rodney P Swartz
(74) Attorney, Agent, or Firm — Birch, Stewart, Kolasch & Birch, LLP

(57) ABSTRACT

The invention relates to methods promoting the aggregation of *Salmonella* bacteria in the gut of subjects, thereby providing immune exclusion and limiting bacterial entry, therefore reducing mucosal and systemic infection.

Figure 1:
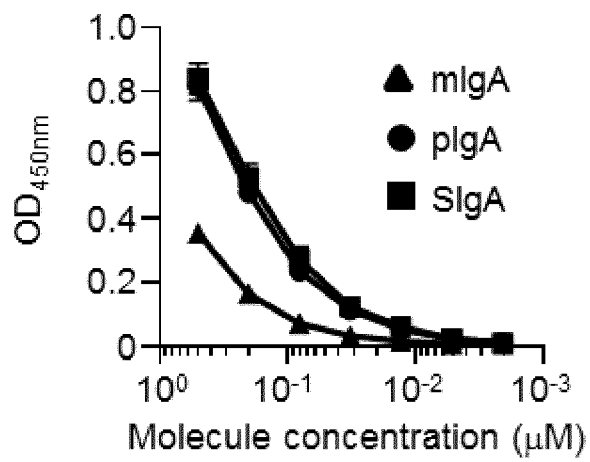
Figure 1:
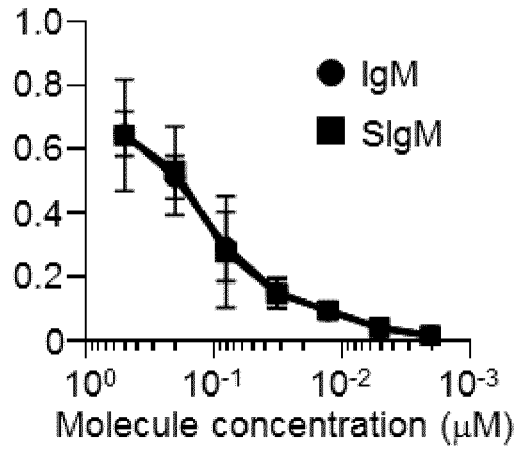
Figure 1:
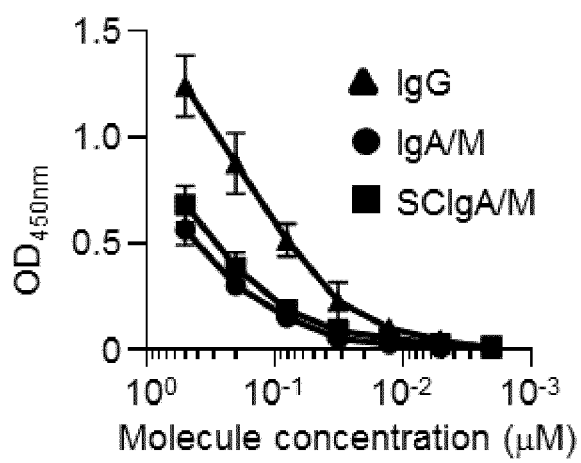
Figure 1:
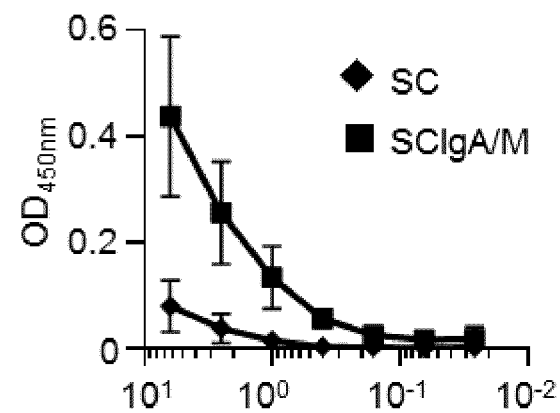

18 Claims, 14 Drawing Sheets
Specification includes a Sequence Listing.

(56) References Cited

OTHER PUBLICATIONS

Longet et al., "Human Plasma—derived Polymeric IgA and IgM Antibodies Associate with Secretory Component to Yield Biologically Active Secretory-like Antibodies", The Journal of Biological Chemistry, vol. 289, No. 31, Aug. 1, 2014, pp. 21617-21626 (11 pages total).

Longet et al., "Reconstituted Human Polyclonal Plasma-derived Secretory-like IgM and IgA Maintain the Barrier Function of Epithelial Cells Infected with an Enteropathogen", The Journal of Biological Chemistry, vol. 289, No. 31, Aug. 1, 2014, pp. 21617-21626 (11 pages total).

Mantis et al., "Secretory IgA's complex roles in immunity and mucosal homeostasis in the gut", Immunology, vol. 4, No. 6, Nov. 2011, pp. 603-611.

Mathias et al., "Agglutinating Secretory IgA Preserves Intestinal Epithelial Cell Integrity during Apical Infection by Shigella flexneri", Infection and Immunity, vol. 81, No. 8, Aug. 2013, pp. 3027-3034.

Michetti et al., "Monoclonal Secretory Immunoglobulin A Protects Mice against Oral Challenge with the Invasive Pathogen *Salmonella typhimurium*", Infection and Immunity, vol. 60, No. 5, May 1992, pp. 1786-1792.

Mikulic et al., "Secretory IgA in complex with Lactobacillus rhamnosus potentiates mucosal dendritic cell-mediated Treg cell differentiation via TLR regulatory proteins, RALDH2 and secretion of IL-10 and TGF-β", Cellular & Molecular Immunology, vol. 14, 2017, pp. 546-556.

Phalipon et al., "Secretory Component: A New Role in Secretory IgA-Mediated Immune Exclusion In Vivo", Immunity, vol. 17, Jul. 2002, pp. 107-115.

Pigny et al., "Intranasal Vaccination With *Salmonella*-Derived Serodominant Secreted Effector Protein B Associated With Gas-Filled Microbubbles Partially Protects Against Gut Infection in Mice", JID, vol. 214, Aug. 1, 2016 (published online Apr. 27, 2016), pp. 438-446.

Pulickal et al., "Kinetics of the Natural, Humoral Immune Response to *Salmonella enterica* Serovar Typhi in Kathmandu, Nepal", Clinical and Vaccine Immunology, vol. 16, No. 10, Oct. 2009, pp. 1413-1419.

Rey et al., "Targeting of Secretory IgA to Peyer's Patch Dendritic and T Cells after Transport by Intestinal M Cells", J. Immunol, vol. 172, 2004, pp. 3026-3033 (9 pages total).

Rindisbacher et al., "Production of Human Secretory Component with Dimeric IgA Binding Capacity Using Viral Expression Systems", The JournaL of Biological Chemistry, vol. 270, No. 23, Issue of Jun. 9, 1995, pp. 14220-14228.

Strugnell et al., "The role of secretory antibodies in infection immunity", Nature Reviews Microbiology, vol. 8, Sep. 2010 (published online Aug. 9, 2010), pp. 656-667.

Virdi et al., "Recombinant IgA production for mucosal passive immunization, advancing beyond the hurdles", Cell. Mol. Life Sci., vol. 73, 2016 (Published online Oct. 28, 2015), pp. 535-545.

World Health Organization, "*Salmonella* (non-typhoidal)", Fact Sheet 139, Feb. 20, 2018, pp. 1-5.

\* cited by examiner

A  Kappa chain detection

B  SC detection

A

B

A

B

A

B

A

B

C

A

Days

B

C

A

B

C

D

A

B

C

METHODS FOR AFFECTING *SALMONELLA* INFECTIONS

The invention relates to methods promoting the agglutination of *Salmonella* bacteria in the gut of subjects, thereby providing immune exclusion and limiting bacterial entry, therefore reducing mucosal and systemic infection.

Protection of mucosal surfaces against colonization and possible entry and invasion by microbes is provided by a combination of constitutive, non-specific substances (mucus, lysozyme and defensins), and also by specific immune mechanisms including secretory Igs (SIgs) at the humoral level (Chairatana and Nolan (2016) Crit. Rev. Biochem. Mol. Biol. 113:1-12; Mantis et al. (2011) Mucosal Immunol. 4:603-611). In vivo, experimental and clinical resistance to infection can be correlated with specific secretory IgA (SIgA) antibodies (Abs) serving as an immunological barrier at mucosal surfaces (Corthésy (2013) Autoimmun. Rev. 12:661-665; Strugnell and Wijburg (2011) Nat. Rev. Microbiol. 8:656-667). It is thought that aggregation, immobilization and neutralization of pathogens at mucosal surfaces is facilitated by the multivalency of SIgA (Mathias et al. (2013) Infect. Immun. 81:3027-3034; Levinson et al. (2015) Infect. Immun. 83:1674-1683). SIgM serving as a surrogate of SIgA in IgA-deficient individuals appears to act via a similar protective mechanism (Brandtzaeg (2009) Scand. J. Immunol. 70:505-515).

The lack of effective vaccines against several infectious agents, and the emergence of new pathogens and problems associated with antibiotic resistance, has led to a renewed interest in passive immunization. Because mucosal surfaces are the major portal of entry for microbes and because their specific neutralization is largely mediated by secretory immunoglobulins, the concept of using exogenously delivered Abs as prophylactic and therapeutic tools has arisen. In emergency situations that cannot wait for a vaccine to produce its effect, direct intervention with Ab molecules to the affected site represents the basis for topical immunotherapy (Virdi et al (2016) Cell Mol. Life Sci. 73:535-545).

We have previously established that polyreactive, serum-derived polymeric IgA, IgM and a mixture of the two isotypes (IgA/M) can be assembled into secretory Abs upon combination with recombinant secretory component (SC) (Longet et al. (2013) J. Biol. Chem. 288:4085-4094). In support of their use for local passive immunization, the molecules display high in vitro stability upon exposure to intestinal washes rich in proteases (Crottet and Corthésy (1998) J. Immunol. 161:5445-5453).

We have now surprisingly shown that immune complexes of large size form between such preparations comprising secretory Igs and the enteropathogen *Salmonella*. Following oral administration of such immunoglobulins, large aggregates keep existing in the intestinal lumen, thus limiting entry of the pathogen into the intestinal target tissue, namely Peyer's patches (PPs) and mesenteric lymph nodes (MLNs). Systemic dissemination assessed in the spleen is diminished as well, resulting in quenching of local inflammatory responses. Such effects were obtained as a function of the dose and molecular form of the Ab administered, with SCIgA/M performing the best. Surprisingly, the exogenously delivered Ab molecules exhibit the same functional features as locally secreted endogenous Abs in the harsh gut environment.

One aspect of the present invention is a method for promoting agglutination of *Salmonella* bacteria in the gut of a subject, comprising administering a composition comprising secretory IgA (SCIgA) and/or secretory IgM (SCIgM) to the gut of the subject, wherein the composition is not milk or derived from milk. Another aspect of the invention is the use of a composition comprising SCIgA and/or SCIgM for promoting agglutination of *Salmonella* bacteria in the gut of a subject, wherein the composition is not milk or derived from milk. Yet another aspect of the invention is a composition comprising SCIgA and/or SCIgM for use in the treatment or prevention of *Salmonella* infection in a subject, wherein the composition is administered to the gut of the subject and promotes agglutination of *Salmonella* bacteria, wherein the composition is not milk or derived from milk.

Preferably, the composition is administered orally to the subject.

Preferably, the agglutination of the bacteria leads to their immune exclusion.

Preferably, the entry of the bacteria into Peyer's patches (PPs) and their diffusion into mesenteric lymph nodes (MLNs) are inhibited. More preferably, the composition reduces mucosal infection. More preferably, the composition reduces local inflammation. Even more preferably, the composition reduces the systemic dissemination of the *Salmonella* bacteria.

Preferably the *Salmonella* bacteria are *Salmonella enterica* subsps, e.g. *Salmonella typhi*.

The composition preferably comprises IgA and/or IgM with binding specificity for *Salmonella* bacteria, preferably for *Salmonella enterica* subsps, even more preferably for *Salmonella typhi*.

Preferably the IgA and/or IgM is prepared from plasma, preferably from human plasma. More preferably, the IgA and/or IgM is combined in vitro with secretory component (SC). More preferably the SC is human secretory component. Even more preferably the SC is recombinant SC, expressed in a mammalian cell line.

Preferably at least 10% of the protein in the composition is SCIgA, more preferably at least 15%, 18%, 20%, or 25%, even more preferably at least 30%, 40% or 50% of the protein in the composition is SCIgA. Preferably at least 10% of the protein in the composition is SCIgM, more preferably at least 15%, 18%, 20% or 25%, even more preferably at least 30%, 40% or 50% of the protein in the composition is SCIgM.

Preferably at least 10% of the protein in the composition is SCIgA and at least 10% of the protein in the composition is SCIgM, more preferably at least 15% is SCIgA and at least 15% is SCIgM, even more preferably at least 20% is SCIgA and at least 20% is SCIgM.

Preferably, the IgA and/or IgM may be enriched for Abs with specificity for *Salmonella*.

The IgA and/or IgM may alternatively be monoclonal or a mixture of two or more monoclonal Abs, with specificity for *Salmonella* bacteria, preferably with specificity for *Salmonella enterica* subsps. In this case, the IgA or IgM is co-expressed with J chain in a cell line, preferably in a mammalian cell line. SC may be co-expressed in the same cell line, or expressed separately and combined with the J chain-comprising dimeric/polymeric IgA/IgM in vitro.

*Salmonella enterica* species comprise as many as 2500 serovars; they comprise 8 subspecies. Around 2000 serotypes induce nontyphoidal disease, including food poisoning. Typhoid fever is caused by *Salmonella* serotypes which are adapted to humans or higher primates. While presently self-contained in developed countries, typhoid fever has a devastating effect in India, in some African countries and generally countries with a poor health care system, lack of clean drinking water and poor hygienic conditions. The risk of death is about 10-30% in infected patients without treatment. Based on WHO fact sheet No. 139, the onset of disease symptoms occurs 6-72 hours after ingestion of *Salmonella*, and illness lasts for up to 7 days. Patients are usually treated with antibiotics, but formerly used antibiotics such as streptomycin, ampicillin and chloramphenicol are no longer used as first line therapy since the emergence of multi-drug resistant typhoid. Antibiotics like ciprofloxacin, ceftriaxone or azithromycin are used, but in general, resistance to antibiotics is an increasing problem, and alternative approaches will be required for the treatment of *Salmonella* infections, in particular of multi-drug resistant *Salmonella* infections, such as multi-drug resistant typhoid.

The invention provides a method to promote agglutination of *Salmonella* bacteria in the gut of subjects, by administering a composition comprising SCIgA and/or SCIgM to the gut of the subject, e.g. by oral administration, wherein the composition is not milk or derived from milk. Surprisingly this leads to the formation of large aggregates of the immunoglobulin and the bacteria, which leads to immune exclusion of the bacteria. Preferably the remaining free *Salmonella* bacteria are reduced by the composition by at least 10%, more preferably by at least 20%, 25%, 30%, 35%, 40%, 45%, 50%, even more preferably by at least 60%, 70%, 75%, most preferably by at least 80%.

The entry of the *Salmonella* bacteria into PPs and the diffusion into MLNs is inhibited by the composition. Preferably the number of colony-forming units (cfu's), i.e. the bacterial count, per mg PP is reduced by administration of the composition by at least 2 fold, more preferably by at least 2.5 fold, 3 fold, even more preferably by at least 4 fold.

The composition also reduces mucosal infection. Dissemination of *Salmonella* is inhibited after administration, preferably oral administration, of the immunoglobulin composition. Bacterial counts in mucosal tissues are preferably reduced by at least 2 fold, more preferably by at least 3 fold, 4 fold, or even 5 fold, even more preferably by at least 6 fold, 7 fold, 8 fold, most preferably by at least 9 fold, when observed 48 hours after administration of the immunoglobulin composition. Bacterial counts in mucosal tissues (PPs and MLNs) and/or the spleen is preferably reduced by at least 2 fold, more preferably by at least 3 fold, 4 fold, or even 5 fold, even more preferably by at least 6 fold, 7 fold, 8 fold, most preferably by at least 9 fold, when observed 6 days after administration of the immunoglobulin composition.

Another aspect of the invention is the prophylactic effect of administration, preferably oral administration, of the immunoglobulin composition. Preferably prophylactic administration of the immunoglobulin composition, e.g. 8 hours or 24 hours prior to the infection, leads to a reduction of bacterial counts in PPs, or MLNs, or spleen, or liver, by at least 2 fold, more preferably by at least 3 fold, 4 fold, or even 5 fold, even more preferably by at least 6 fold, 7 fold, 8 fold, most preferably by at least 9 fold, when observed 6 days post infection, as compared to without administration of the immunoglobulin composition.

Preferably, administration, preferably oral administration, of the immunoglobulin composition prior to infection (i.e. prophylactic administration, e.g. 8 or 24 hours prior to the infection) reduces weight loss caused by the infection by at least 20%, more preferably by at least 30%, 40%, or 50%, even more preferably by at least 60%, most preferably by at least 70%.

Local inflammation is also reduced. Preferably the frequency of neutrophils observed in PPs is reduced by administration, preferably oral administration, of the immunoglobulin composition by at least 10%, 20%, more preferably by at least 25%, 30%, 40%, even more preferably by at least 50%, most preferably by at least 60%. Preferably the frequency of macrophages observed in PPs is reduced by administration, preferably oral administration, of the immunoglobulin composition by at least 10%, 20%, more preferably by at least 25%, 30%, 40%, even more preferably by at least 50%, most preferably by at least 60%. Preferably the secretion of pro-inflammatory cytokines, e.g. TNF-alpha or IL-6, is reduced by at least 2 fold, more preferably by at least 2.5 fold, even more preferably by at least 3 fold 6 days after administration, preferably oral administration of the immunoglobulin composition.

Another aspect of the invention is the therapeutic effect of the immunoglobulin composition. Preferably, therapeutic administration of the immunoglobulin composition, e.g. one hour after the infection, leads to a reduction of bacterial counts in PPs, or MLNs, or spleen, or liver, by at least 2 fold, more preferably by at least 3 fold, 4 fold, or even 5 fold, even more preferably by at least 6 fold, 7 fold, 8 fold, most preferably by at least 9 fold or even at least 10 fold, when observed 6 days post infection, as compared to without administration of the immunoglobulin composition.

Preferably, therapeutic administration, preferably oral administration, of the immunoglobulin composition (e.g. 1 hour or 8 hours after the infection) reduces weight loss caused by the infection by at least 20%, more preferably by at least 30%, 40%, or 50%, even more preferably by at least 60%, most preferably by at least 70%.

Preferably the IgA and/or IgM is prepared from plasma, as described in detail, for example, in WO 2013/132053.

The immunoglobulin composition preferably used in the present invention can be prepared as described in detail in WO 2013/132052. Preferably, plasma derived preparations comprising IgA and/or IgM are combined in vitro with SC, without requiring prior purification of the dimeric/polymeric J chain containing IgA/IgM. Such material is referred to as secretory-like IgA or secretory-like IgM, or abbreviated as SCIgA or SCIgM. However, this material behaves very similarly to in vivo produced secretory IgA (usually abbreviated SIgA) and in vivo produced secretory IgM (usually abbreviated SIgM).

The term "secretory component" as used herein refers to a protein that specifically binds to J chain-containing immunoglobulin, and is related to or derivable from or identical to an extracellular portion of the polymeric immunoglobulin receptor (pIgR), preferably a mammalian pIgR, more preferably a primate pIgR, most preferably a human pIgR. Preferably, the secretory component confers increased stability to the J chain containing immunoglobulin. SC comprised in the composition may be recombinant SC, preferably SC produced in a mammalian cell line. SC in its traditional, narrow meaning (referred to as "natural SC" herein) is the extracellular portion of the pIgR, which usually gets associated during secretion with dimeric or polymeric IgA or pentameric IgM comprising a J chain. J chain-containing IgA/IgM binds to the polymeric immunoglobulin receptor at the basolateral surface of epithelial cells and is taken up into the cell by endocytosis. This receptor complex then transits through the cellular compartments before being transported to the luminal surface of the epithelial cells. The transcytosed IgA/IgM-pIgR complex is then released through proteolysis, and part of the pIgR, referred to as the natural SC, stays associated with the J chain-containing IgA/IgM, releasing SIgA/SIgM. However, there is evidence that reverse transcytosis of SIgA, i.e. from the luminal surface to the basolateral surface, can also take place.

The human pIgR is cloned and sequenced, its sequence is available as SwissProt entry P01833, and shown in Seq ID NO: 1. Human pIgR is a glycoprotein with 764 amino acid residues, containing a signal peptide (residues 1 to 18), an extracellular part (residues 19 to 638), a transmembrane region (residues 639 to 661), and a cytoplasmic region (residues 662 to 764). Residues 19 to 603 are thought to associate with J chain-containing IgA as described above, and this part of this glycoprotein is usually referred to as the SC (referred to as "natural SC" herein).

SC used in the immunoglobulin composition used in the present invention can comprise any extracellular pIgR sequence that is capable of associating with J chain-containing IgA. For example, SC may comprise extracellular domains of pIgR from mammalian sources, e.g. from primates, cattle, horses, cats, dogs, rabbits, guinea pigs, rats or mice, or variants thereof. Functional hybrids of the extracellular domains from several mammalian species or variants thereof are also contemplated for use in the invention, e.g. prepared by fusing the immunoglobulin-like domains from different species into a SC-like protein. A functional SC may also be formed by fusing a selection of immunoglobulin-like domains normally present, e.g. rabbit SC is functional being composed of only domains 1, 4 and 5. Preferably, however, the human SC or functional variants thereof is used.

Therefore the SC used in the immunoglobulin composition used in the invention preferably comprises residues 19 to 603 of SEQ ID NO: 1 or functional variants thereof. Functional variants may include deletions, insertions, and/or substitutions, preferably substitutions are conservative substitutions, e.g. a basic amino acid residue is substituted for another basic amino acid, a hydrophobic amino acid is substituted for another hydrophobic amino acid, etc. The variant SC is at least 50% identical in sequence to residues 19 to 603 of SEQ ID NO: 1, preferably at least 55%, 60%, 65%, 70%, 75%, 80%, more preferably at least 85% or even 90%, even more preferably at least 92%, 94%, 95%, 97%, 98%, or even 99% identical to residues 19 to 603 of SEQ ID NO: 1. Preferably, the SC comprises the extracellular portion of the pIgR, more preferably the extracellular portion of the human pIgR, most preferably the SC comprises or even consists of residues 19 to 603 of SEQ ID NO: 1.

The skilled person is well aware how to produce the SC by recombinant techniques. An example of expression of human SC in CHO cells has been described by Phalipon et al (Phalipon et al., (2002) Immunity 17:107-115), but the invention is not limited to SC produced by this system. For example, the desired cDNA sequence can be produced synthetically or cloned via RT-PCR, using RNA isolated from cells or tissue expressing pIgR as template. The cDNA can then be inserted into a mammalian expression vector such as pcDNA3—many alternative expression vectors are available. The recombinant expression vector will then be introduced into a suitable host cell line, such as CHO, COS-1 or COS-7, HEK293, or BHK. Other cell lines are available and can also be used. Methods for introducing such vectors into a cell line include lipofection, electroporation and other techniques well known to the skilled person. Usually cells harboring the expression vector and expressing the protein of interest are then selected and cloned. Viral expression systems can also be used, for example, vaccinia virus can be used to express proteins at high levels in mammalian cells, baculovirus expression systems can be used to express proteins at high levels in insect cells. Yeast or bacterial expression systems can also be envisaged, and such expression systems are known to the skilled person. Likewise, plant expression systems can also be envisaged, and such systems are known to the skilled person.

SC or variant thereof used in the composition of the invention may also comprise a tag, such as a hexa-Histidine tag, which can aid in the purification of the resulting protein. If such a tag is attached via a cleavable linker, the tag may be cleaved off prior to use in the invention. Similarly, the SC may be produced as a fusion protein. Again, a cleavable linker may be used so that the fusion partner may be cleaved off the SC prior to use in the invention.

The skilled person can then purify the expressed protein with standard methods. Recombinant SC may be purified to high purity with a suitable method, for example size-exclusion and/or ion exchange chromatography. Preferably the final preparation of recombinant SC will be essentially free of contaminants, particularly host cell proteins. However, SC can also specifically associate with J chain containing immunoglobulin in unpurified form, thus purification prior to association with the J chain-containing immunoglobulin is not essential.

The SC may also be obtained from a natural source, preferably from milk, saliva or mucus. Preferably the SC is of human origin, but SC from other species can also be used in the invention.

The molar ratio between SC and J chain containing IgA dimers/polymers or IgM pentamers in the composition of step (a) ranges between 1:10 and 10:1, preferably between 1:5 and 5:1, more preferably between 1:2 and 2:1.

The molar ratio between SC and J chain within the composition of step (a) is between 1:10 and 10:1, preferably between 1:5 and 5:1, more preferably between 1:2 and 2:1.

The amount of SC used in step (b) may be at least 1 part (by weight) of SC to 50 parts (by weight) of protein in the composition of step (a), preferably at least 1 part to 40, 30, 20, 15, 10, most preferably at least 1 part of SC to 5 parts of protein in the composition of step (a).

Alternatively the IgA and/or IgM may be monoclonal anti-*Salmonella* Abs. In the composition used in the invention, a single monoclonal Ab or a mixture of one or more monoclonal Abs may be used. It may be a mixture comprising monoclonal Abs specific for different *Salmonella* species. The monoclonal IgA and/or IgM is then co-expressed with J chain, in a cell, preferably a mammalian cell. Following expression, the resulting J chain containing IgA and/or IgM is then combined in vitro with SC as described for plasma-derived IgA and/or IgM above. However, SCIgA and/or SCIgM can also be produced by co-expressing IgA or IgM, J chain and SC in the same cell (see, for example, U.S. Pat. No. 6,300,104 B1).

Administration is preferably orally.

Determination of the appropriate doses of the immunoglobulin composition for treating or preventing *Salmonella* infections is well within the capabilities of those skilled in the art. For example, a dose of 0.1 g to 10 g, preferably a dose of 0.2 g to 5 g, more preferably a dose of 0.5 g to 2 g, even more preferably a dose of 1 g is administered. Preferably the dose is administered four times per day, more preferably three times per day, even more preferably twice per day, most preferably once per day, as long as symptoms of the infection are present, preferably a dose of 1 g once per day could be used.

Alternatively a dose of 1 to 100 mg/kg bodyweight could be administered, preferably 1 to 50 mg/kg, even more preferably 5 to 20 mg/kg, most preferably 10 to 15 mg/kg.

Preferably the immunoglobulin composition is administered during the acute phase of the disease, for example for as long as the patient shows disease symptoms such as fever, diarrhea, abdominal pain, headaches, and/or as long as bacteria can be found in blood and/or stool.

Another aspect of the invention is the use of the immunoglobulin composition as described above as treatment in addition to standard antibiotic treatment. For this aspect of the invention the immunoglobulin is administered as described above to assist the antibiotics in eliminating the *Salmonella* bacteria from the patient. For example, the immunoglobulin composition is administered using the same dosage as outlined above during the acute phase of the infection while the patient is receiving antibiotic therapy. Preferably, the immunoglobulin composition is administered during the first two days, more preferably during the first three days, even more preferably during the first four days, most preferably during the first five days of infection, in addition to standard antibiotic therapy.

The invention also provides a method to prevent *Salmonella* infection by administration of the immunoglobulin composition as described above. For example, when travelling into a country with poor hygienic conditions, a dose of 0.1 g to 10 g, preferably a dose of 0.2 g to 5 g, more preferably a dose of 0.5 g to 2 g, even more preferably a dose of 1 g is administered. Preferably the dose is administered twice per day, more preferably once per day, preferably a dose of 1 g once per day could be used. However, the dose can be adjusted, depending on the risk of exposure to *Salmonella* and the likely bacterial load to be encountered. Another aspect of the invention is the use of the immunoglobulin composition as described above for the prevention of *Salmonella* infection. Yet a further aspect of the invention is the immunoglobulin composition as described above for the use of prevention of *Salmonella* infection. The doses that can be used prophylactically are as outlined above.

Preferably the immunoglobulin composition is formulated as a liquid, for example a syrup. For example, it may be a liquid comprising 1 to 20% immunoglobulin, preferably 2 to 20% immunoglobulin, more preferably 2 to 15% immunoglobulin, even more preferably 5 to 10% immunoglobulin. Most preferably, it comprises 5% or 10% immunoglobulin. The liquid preferably also comprises a stabilizer, such as an amino acid (e.g. proline, glycine, histidine, arginine), a saccharide, or a sugar alcohol, or a protein such as albumin; other stabilizers that can be used are well known to the skilled person. The liquid may additionally comprise agents that enhance the taste, such as flavouring. The skilled person will be well aware of how to select suitable excipients and taste-enhancing agents.

Alternatively, the immunoglobulin composition may be administered in form of a capsule, preferably an acid-resistant capsule that releases its content in the gut of the subject. The skilled person will be well aware of how to prepare such dosage forms.

Alternatively, the immunoglobulin composition may be administered in form of a gel or a powder.

In fact, any form that can be taken orally can be envisaged.

LIST OF FIGURES

FIG. 1. Plasma-derived Ab formulations interact with St. Binding of equimolar concentrations of (A) plasma-derived Abs or (B) recombinant SC or SCIgA/M to coated *S. enterica* serovar *Typhimurium* (St) as determined by ELISA. Data are the compilation of four independent experiments performed in duplicates, and are depicted as means+/− standard deviation.

Figure 2:
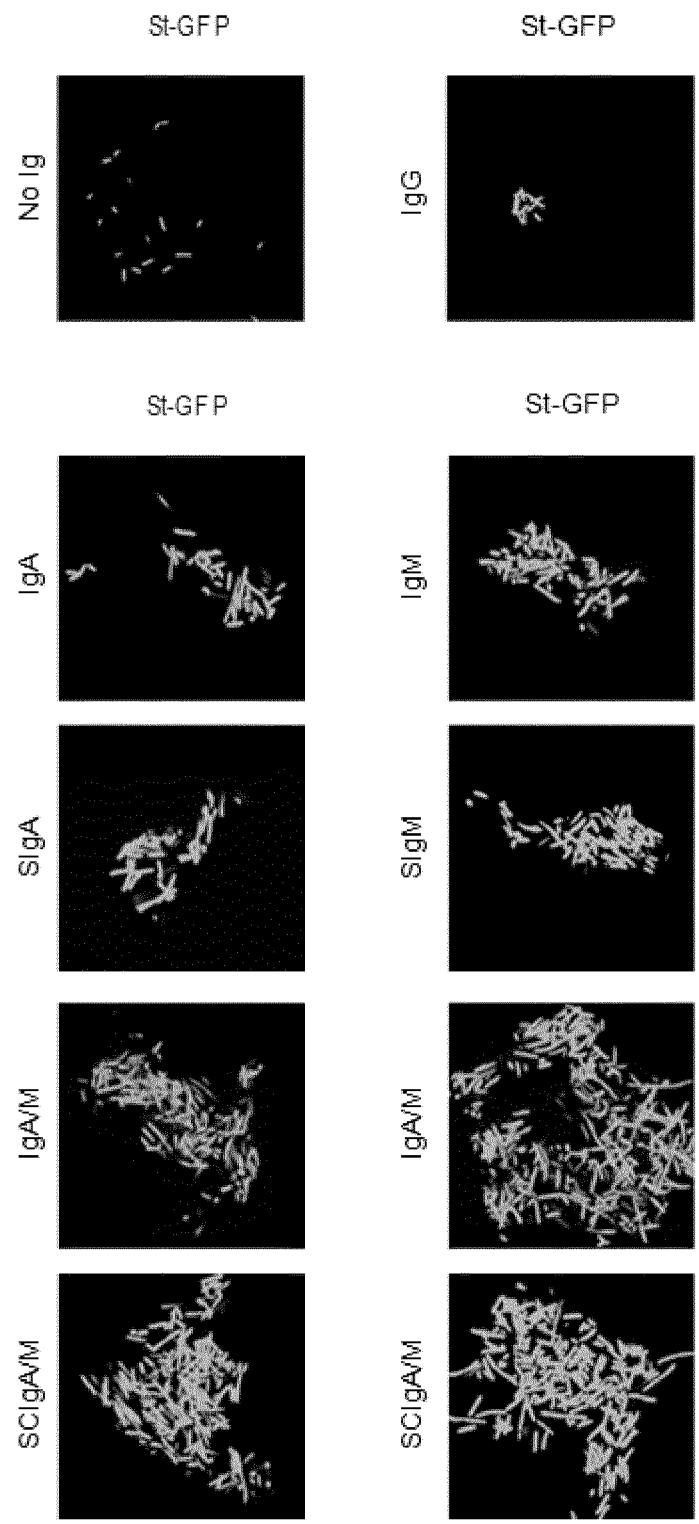

FIG. 2. Association of plasma-derived Ab formulations with St promotes agglutination. Laser scanning confocal microscopy images of immune complexes of St associated with plasma-derived Abs. Bacteria constitutively expressing green fluorescent protein (GFP) are shown. Images are representative of one observed field obtained from 5-10 observations from three independent slides.

Figure 3:
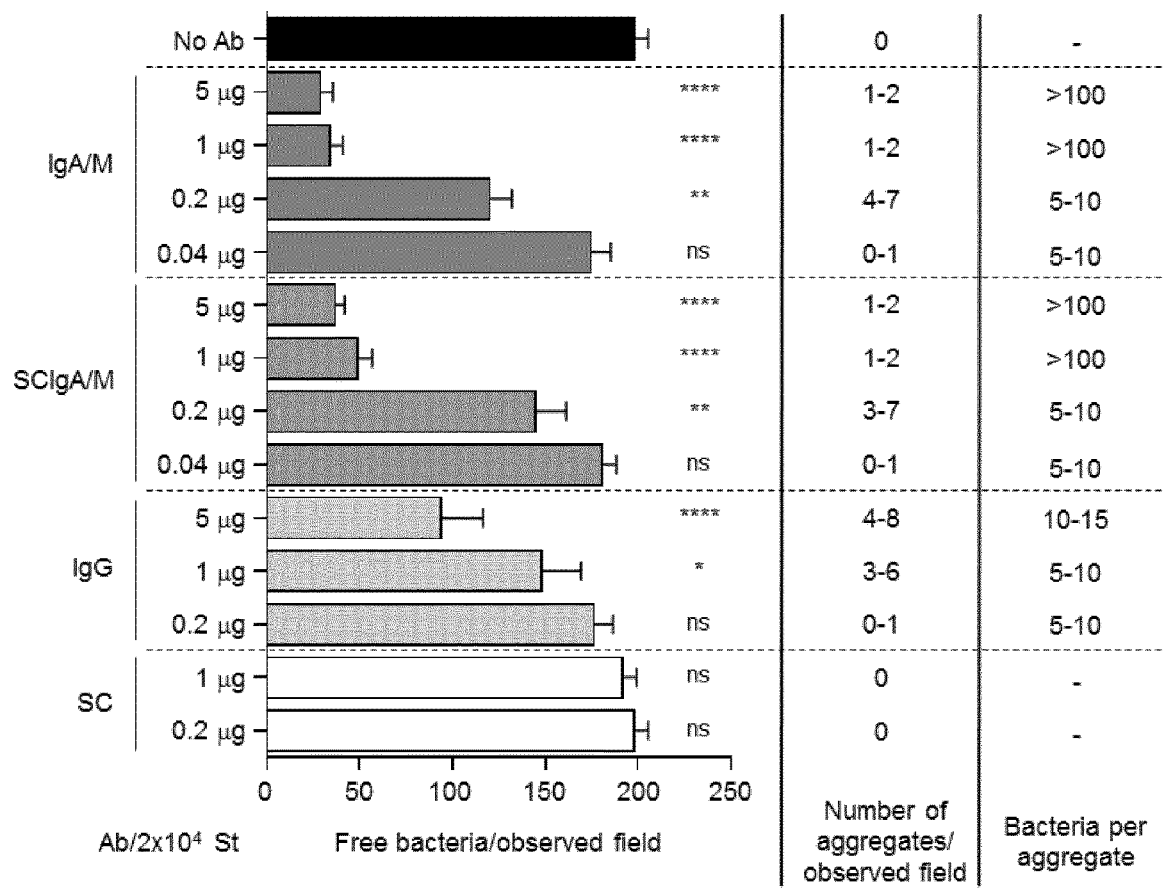

FIG. 3. Quantification of the agglutination property of IgAM, SCIgAM, IgG Abs or SC. $2 \times 10^7$ St alone or in combination with decreasing amounts of protein formulations were observed by laser scanning confocal microscopy. Using the Imaris 8 software, parameters including the number of free fluorescent bacteria, the number of aggregates, and the estimated number of bacteria per aggregate were evaluated on 10 different fields from one experiment repeated 5 times. Numbers are means+/−standard deviation. Statistical analyses were performed by comparison with the "No Ab" experimental group.

Figure 4:
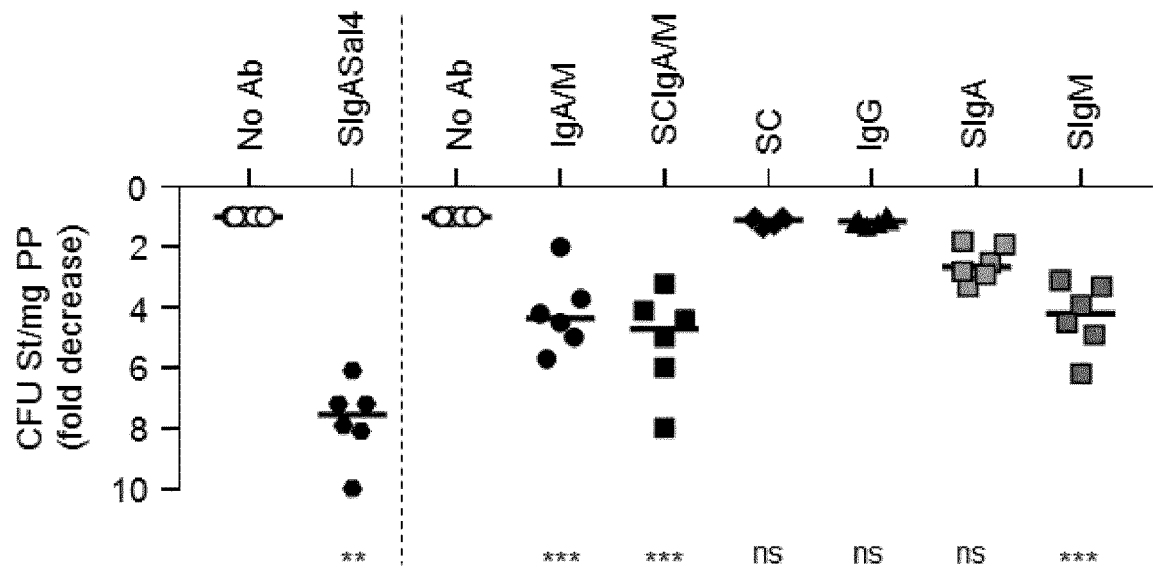

FIG. 4. Reduction of St entry into PPs by Ab preparations following delivery in a ligated intestinal loop. $2 \times 10^6$ St were administered alone or in the presence of IgA/M, SCIgA/M, SC, IgG, SIgA, SIgM, and SIgASal4 as a positive control into an ligated intestinal loop containing a PP. At 1.5 hour, PPs were collected, lysed and bacterial counts were determined by plating. Data are presented as fold decrease with respect to the "No Ab" experimental group. Data are depicted as means+/−standard deviation.

Figure 5:
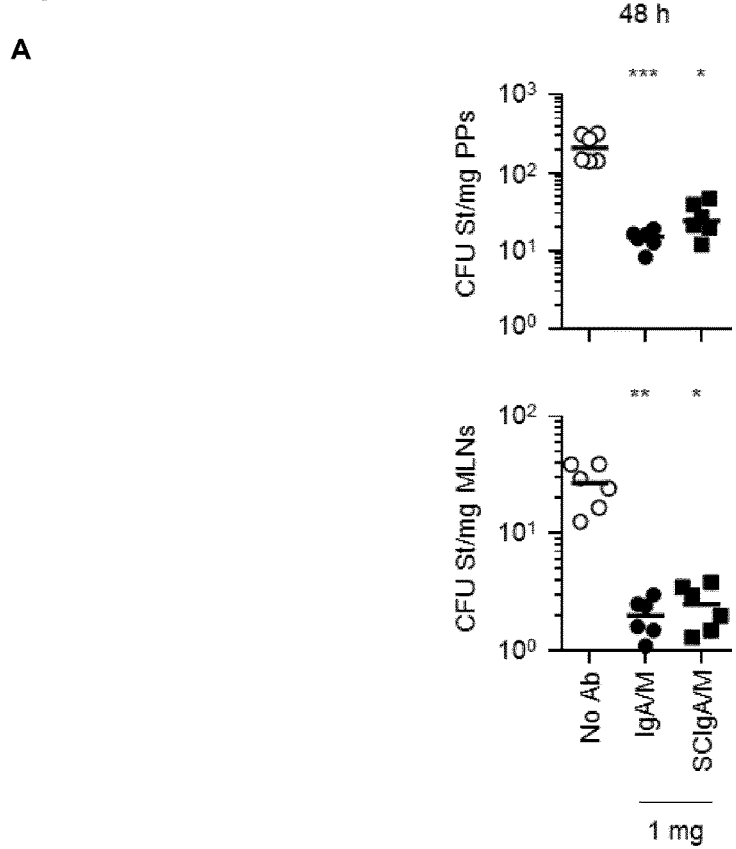
Figure 5:
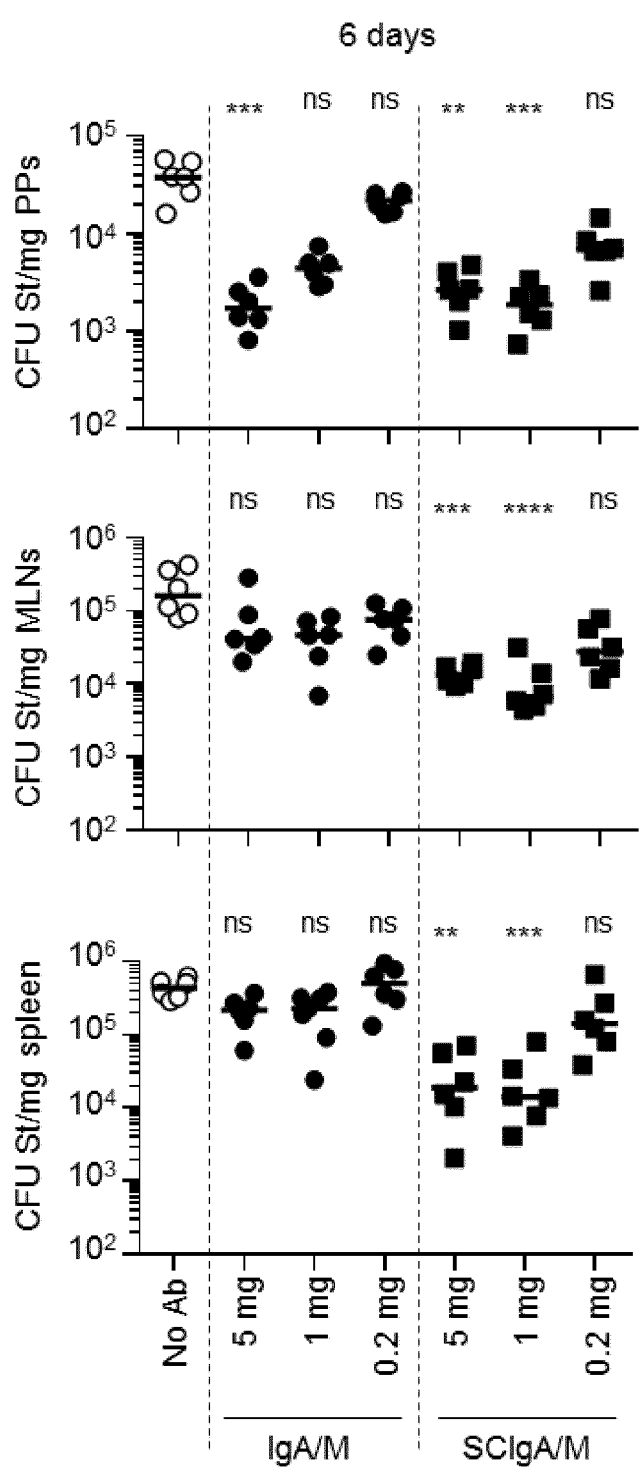

FIG. 5. Limitation of St dissemination in the presence of Ab formulations after oral administration. Mice were orally administered $2 \times 10^7$ St alone or in association with preparations IgA/M, SCIgA/M or IgG. (A) Bacterial counts in mucosal tissues (PPs, MLNs) were determined by plating of tissue lysates 48 hours post-delivery of St or immune complexes prepared in the presence of 1 mg Abs. (B) Similar experiment as in (A), using immune complexes made of $2 \times 10^7$ St and decreasing amounts of Abs, with bacterial counts assessed in PPs, MLNs and the spleen at day 6 post-administration. Experiments were performed twice, with 3 mice per group, and the compilation of the two experimental sets is depicted. Data are depicted as means+/− standard deviation. Statistical analyses were performed by comparison with the "No Ab" experimental group.

Figure 6:
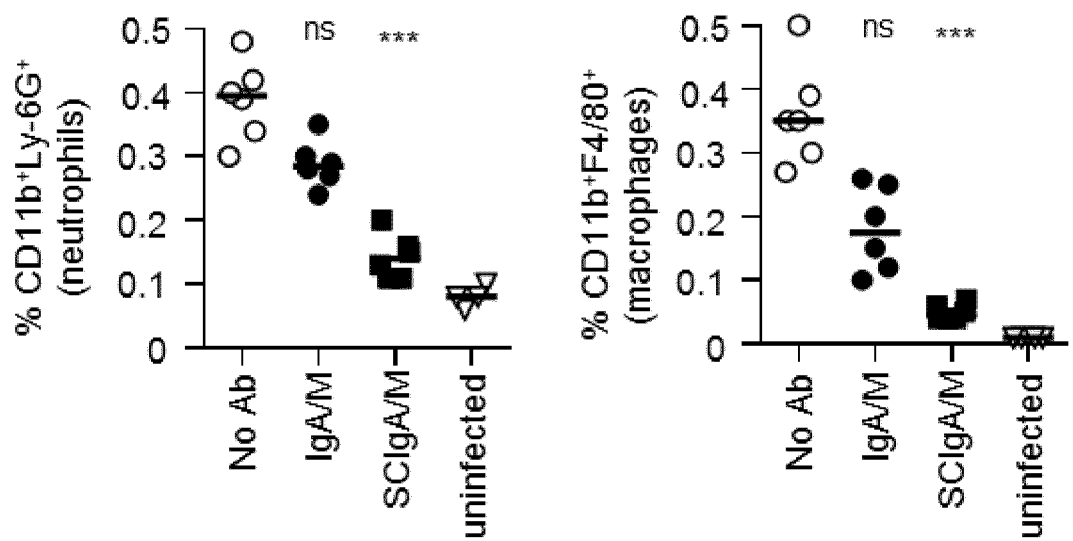
Figure 6:
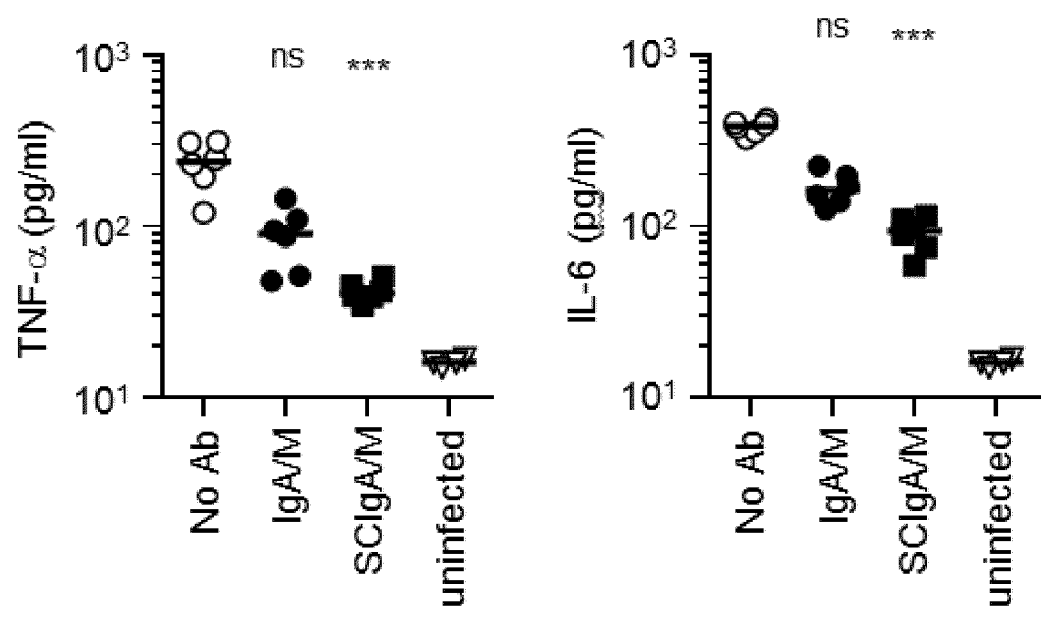

FIG. 6. Reduced markers of inflammation after oral delivery of St in the presence of Ab formulations. (A) Frequency of neutrophils and macrophages in PPs determined 6 days post-administration of $2 \times 10^7$ St alone or in association with 1 mg of IgA/M or SCIgA/M preparations. (B) Pro-inflammatory cytokine secretion measured in cell culture suspensions of PPs from the same experimental groups as in (A). Experiments were performed twice, with 3 mice per group, and the compilation of the two experimental sets is depicted. Data are depicted as means+/−standard deviation. Statistical analyses were performed by comparison with the "No Ab" experimental group.

Figure 7:
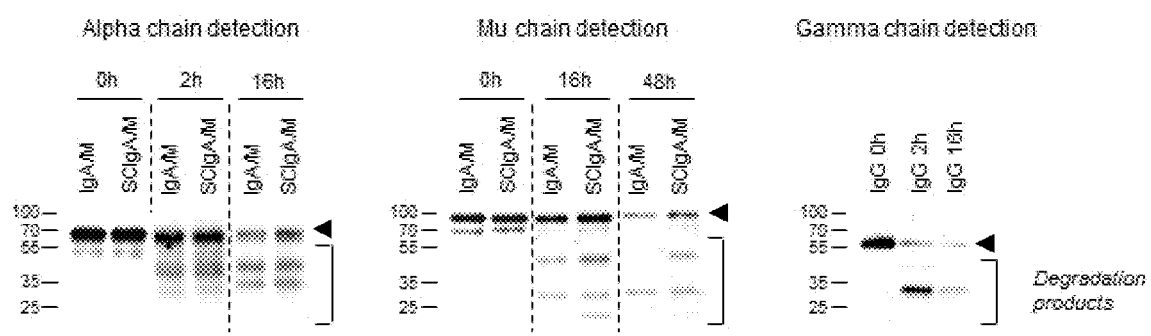
Figure 7:
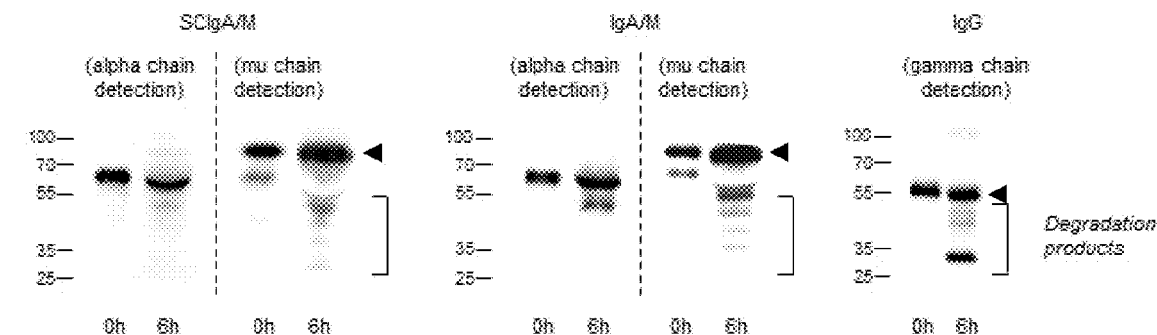

FIG. 7. Location and stability of Ab formulation in the GI tract. (A) In vitro digestion patterns observed at three time points of IgA/M, SCIgA/M and IgG incubated with intestinal washes, as assayed by immunodetection of the respective heavy chain under reducing conditions. The position of the intact alpha, mu and gamma chains is indicated by an arrowhead. (B) SCIgA/M, IgA/M and IgG incubated for 6 hours in a ligated intestinal loop were recovered as described in Materials and Methods, and analyzed as under (A).

Figure 8:
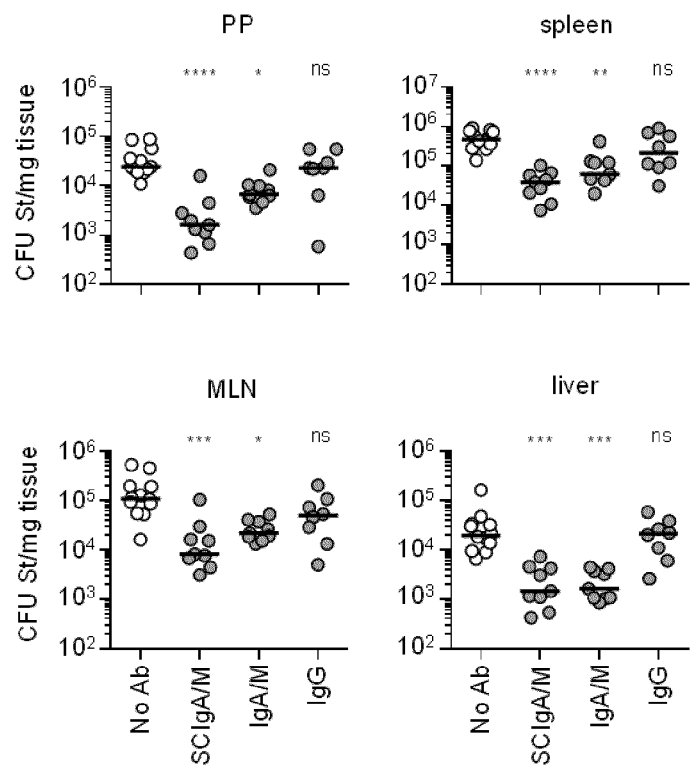
Figure 8:
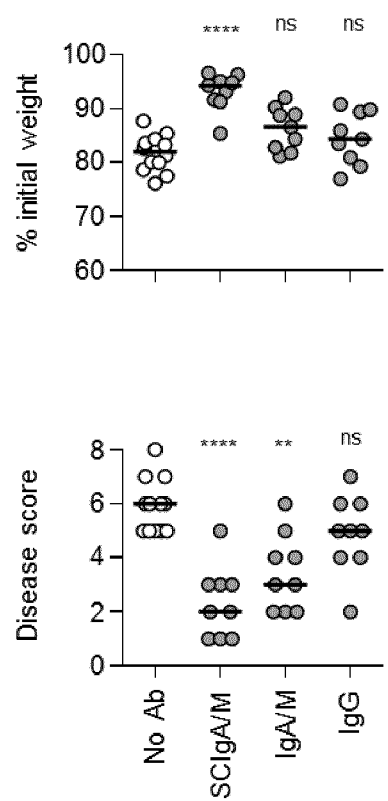
Figure 8:
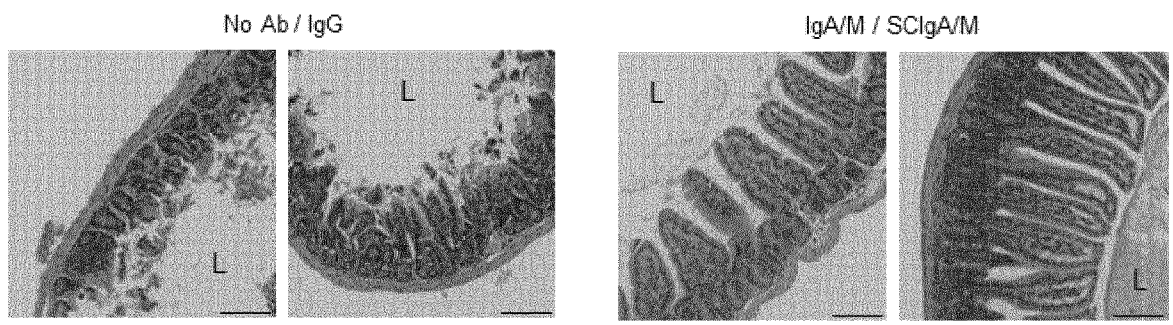

FIG. 8. Prophylactic administration of SCIgA/M preparation limits St entry and reduces symptoms. (A) Bacterial counts measured 6 days post-infection with $2 \times 10^7$ St in Peyer's patch (PP), mesenteric lymph node (MLN), spleen and liver from mice orally administered various formulations of Abs 24 and 8 hours prior to oral infection. Statistical significance were obtained by comparing experimental groups with the "no Ab" condition. (B) Weight loss and disease score (see Materials and Methods) determined at day 6 post-infection as a function of the Ab formulation administered prophylactically. (C) SIgAC5 prevents St-induced destruction of the intestinal barrier. Histologic examination (H&E staining) of intestinal tissue sections obtained from mouse ligated intestinal loops 1 hour post-administration with a single dose of either $2 \times 10^7$ St alone, or in combination with the indicated Ab preparation. Typical examples of results of histological analysis of more than 10 samples are shown. L, Lumen. Magnification, ×100 for all images.

Figure 9:
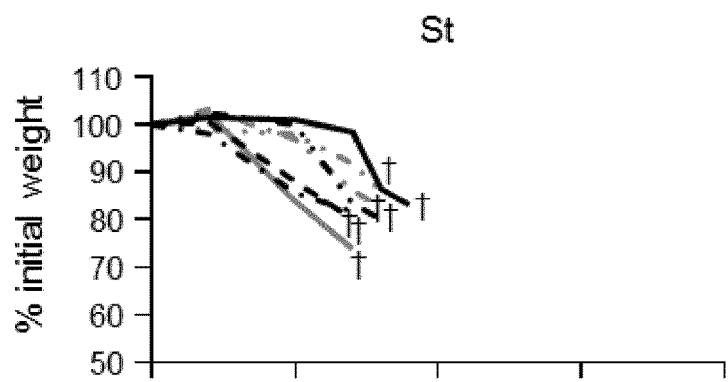
Figure 9:
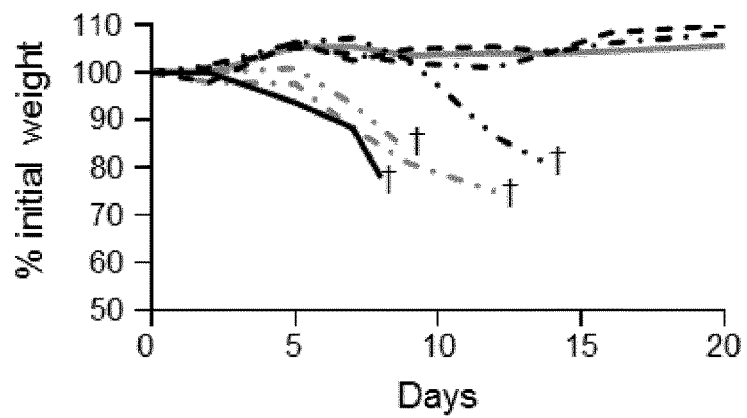
Figure 9:
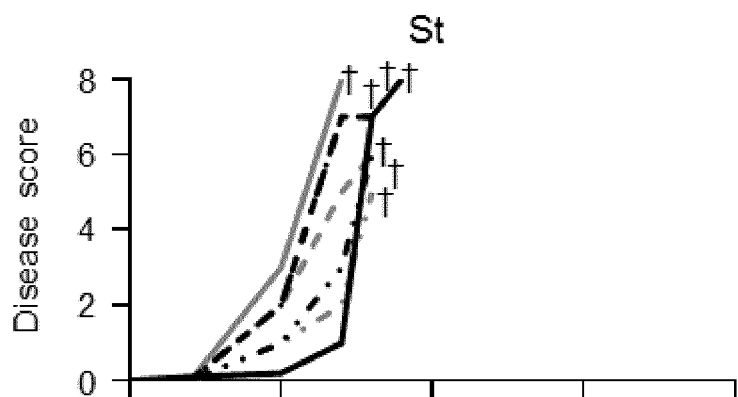
Figure 9:
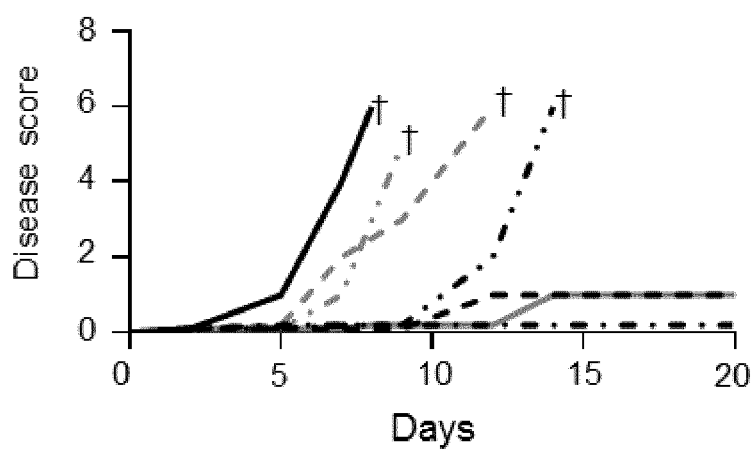
Figure 9:
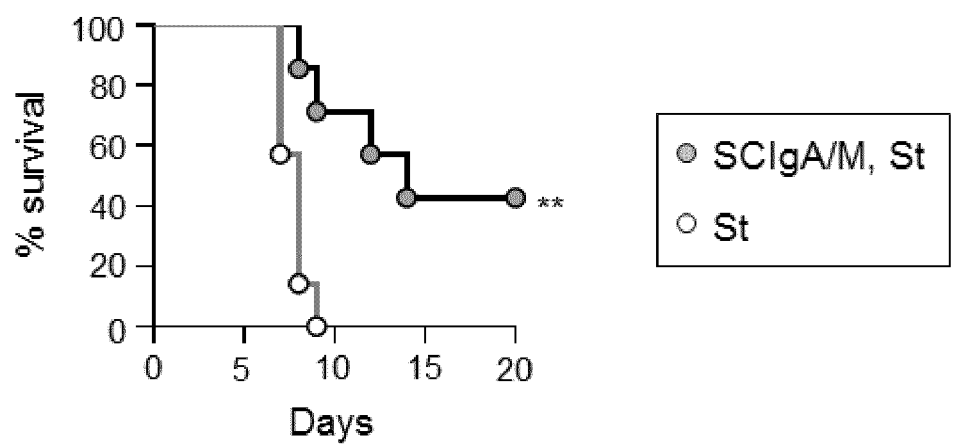

FIG. 9. Prophylactic administration of SCIgA/M preparation promotes mouse survival. Time-dependent follow-up of mice infected with $2 \times 10^7$ St post-prophylactic treatment with two oral delivery of the SCIgA/M preparation. Depicted curves were produced from individual mouse analyzed for weight loss (A) and disease scores (B). Sacrifice (depicted by a †) of mice having lost ≥20% of their initial weight was done to comply with the Veterinary Office's permit to conduct animal experiments. (C) Survival curves resulting from the compilation of all mice in either the St alone group (open circles) or the prophylactic (SCIgA/M, St) group (grey circles).

Figure 10:
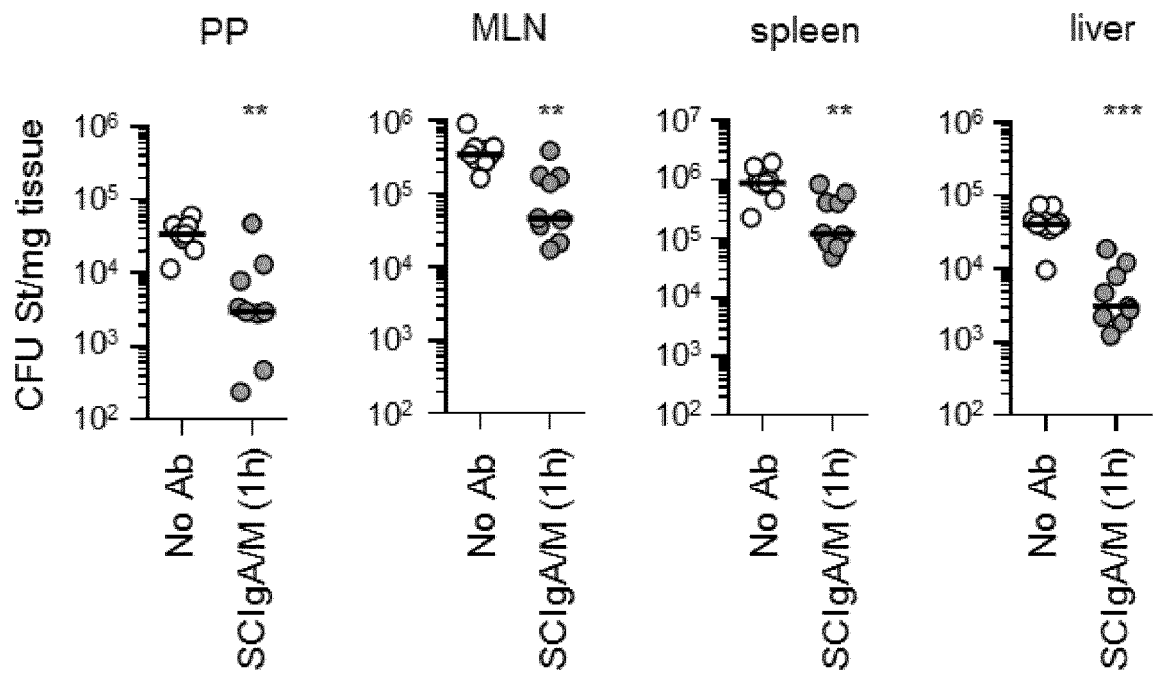
Figure 10:
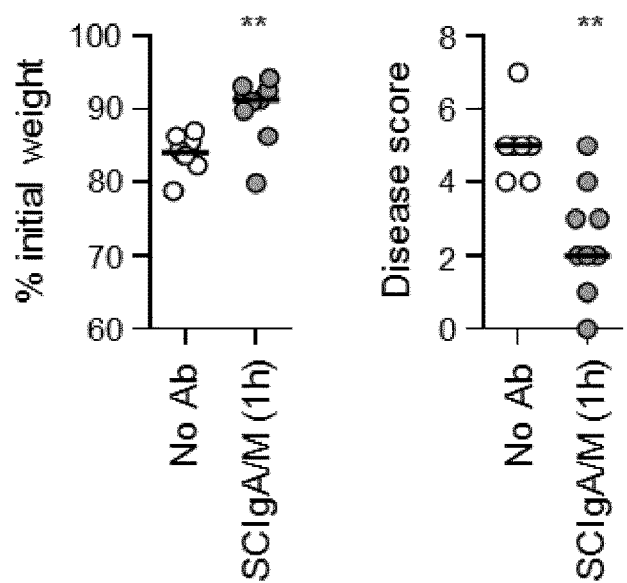
Figure 10:
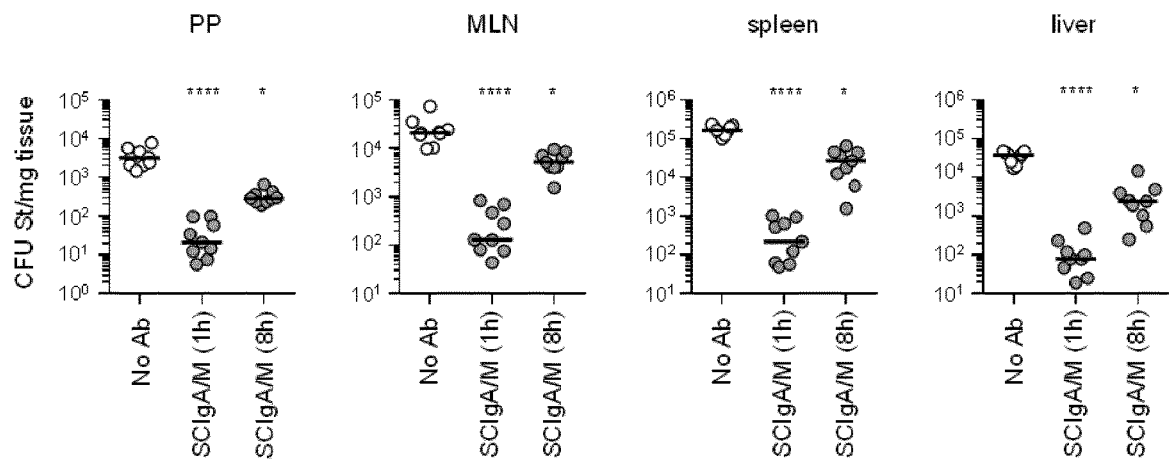
Figure 10:
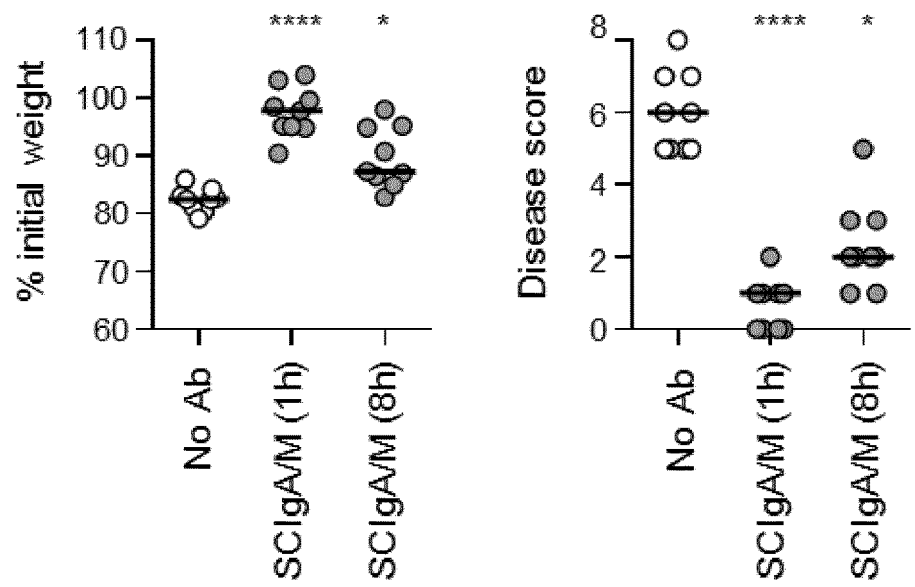

FIG. 10. Therapeutic administration of SCIgA/M limits St entry and reduces symptoms. (A) Bacterial counts measured 6 days post-infection with $2 \times 10^7$ St in PP, MLN, spleen and liver from mice orally administered SCIgA/M 1 hour after oral infection. (B) Weight loss and disease scores (see Materials and Methods) determined at day 6 post-infection of mice treated therapeutically with SCIgA/M as in (A). (C) and (D) Same experiments as in (A) and (B) with infection performed with $2 \times 10^6$ St, followed by subsequent therapeutic oral administration of SCIgA/M 1 or 8 hours after oral infection.

Figure 11:
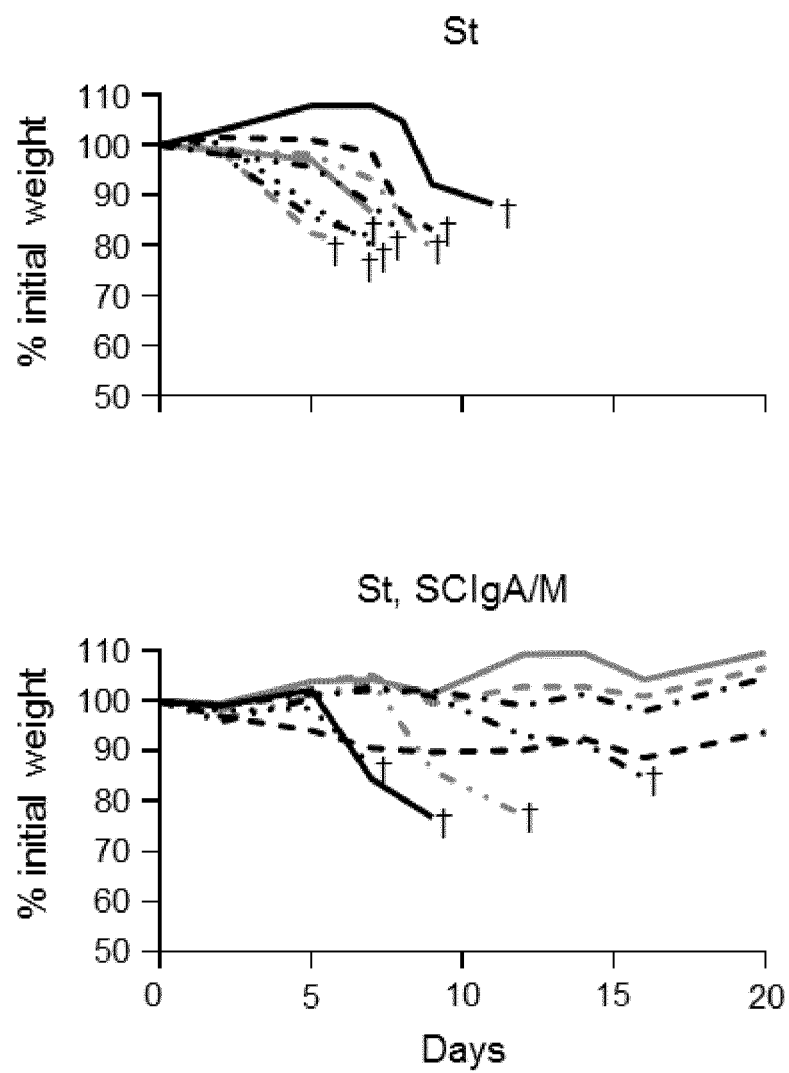
Figure 11:
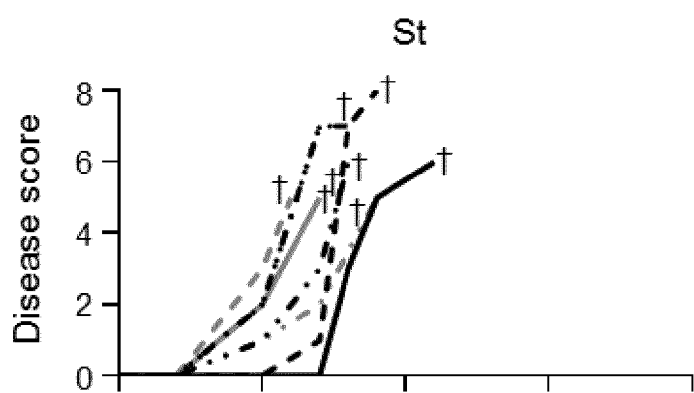
Figure 11:
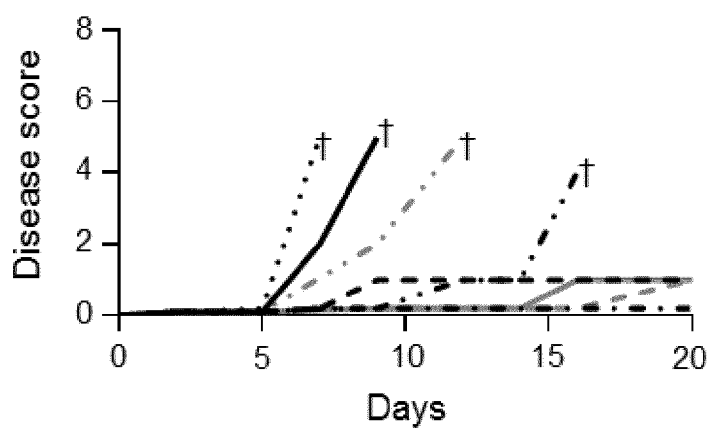
Figure 11:
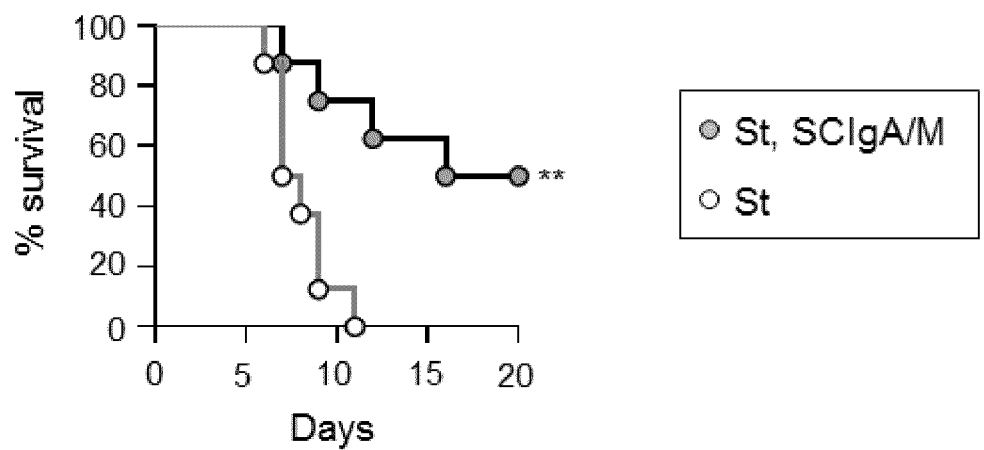

FIG. 11. Therapeutic administration of SCIgA/M preparation promotes mouse survival. Time-dependent follow-up of mice infected with $2 \times 10^6$ St prior to therapeutic treatment carried out 8 hours post-infection with a single dose of the SCIgA/M preparation. Depicted curves were produced from individual mouse analyzed for weight loss (A) and disease scores (B). Sacrifice (depicted by a †) of mice having lost ≥20% of their initial weight was done to comply with the Veterinary Office's permit to conduct animal experiments. (C) Survival curves resulting from the compilation of all mice in either the St alone group (open circles) or the therapeutic (St, SCIgA/M) group (grey circles).

EXAMPLES

The following examples are intended to exemplify, but not limit the invention.

Materials and Methods
Preparation of Human Plasma-Derived and Mouse Monoclonal Abs Human plasma-derived IgG preparations (IgPro10, Privigen) were prepared as reported (Cramer et al. Vox Sang 2009; 96:219-25). Preparations containing IgA and IgM were obtained from an ion-exchange chromatographic side fraction used in the large-scale manufacture of IgG from human plasma. The elution fraction containing IgA and IgM was concentrated and re-buffered to 50 g/l protein in PBS by tangential-flow filtration (TFF; Pellicon XL Biomax 30, Merck Millipore). The resulting IgA/M solution, which contained IgA and IgM in a 2:1 mass ratio, was further processed to: (i) SCIgA/M, by combining in vitro IgA/M with recombinant human SC (Phalipon et al., Immunity 2002; 17:107-15); (ii) polymeric IgA (pIgA) at >50% (by mass), through removal of IgM from IgA/M by affinity chromatography specific for human IgM (CaptureSelect® IgM, BAC B.V., Naarden, Netherlands); (iii) IgM, through removal of IgA from IgA/M by affinity chromatography specific for human IgA (CaptureSelect® IgA). The secretory counterpart of pIgA and IgM was prepared by combination with recombinant human SC (Phalipon et al., Immunity 2002; 17:107-15). Mouse monoclonal secretory IgASal4 (SIgASal4) specific for *S. enterica* Typhimurium surface carbohydrates was prepared as described previously (Michetti P et al Infect Immun 1992; 60:1786-92). Ab preparations were labeled with Cyanin 5 (Cy5) fluorescent dye (Innova Biosciences Ltd) according to the manufacturer's protocol.

Bacterial Strain and Culture Conditions

Bacteria used were the virulent strain SL1344 of *S. enterica* serovar Typhimurium (abbreviated St; Hoiseth S K, Stocker B A. Nature 1981; 291:238-9). Bacteria from frozen stock were grown on Luria-Bertani (LB) agar plates containing 90 µg/ml streptomycin (Sigma-Aldrich) for 24 hours at 37° C. Colonies were amplified in 3 ml of LB liquid broth supplemented with 90 µg/ml streptomycin for 16 hours at 37° C., with shaking. 25-fold dilution of the overnight culture was pursued for 1.5 hour at 37° C. to yield bacteria in the exponential phase. Bacterial density was determined with the knowledge that 1 $OD_{600nm}$ corresponds to $9.5 \times 10^8$ cfu/ml. In specific experiments, the GFP-expressing St strain obtained in the laboratory was prepared under the same conditions, except that 50 µg/ml ampicillin was added for culture.

ELISA

Assessment of the interaction between St and human plasma-derived Abs was carried out by ELISA as described in Longet et al. (J Biol Chem 2014; 289:21617-26) with minor modifications: Serial dilutions of human plasma-derived monomeric IgA (mIgA), polymeric IgA (pIgA), SIgA, IgM, SIgM, IgA/M, SCIgA/M or IgG (starting at 0.5 µM) or SC (starting at 6.25 µM) were added to St coated in PBS. Bound proteins were detected by incubation with biotinylated goat anti-human kappa chain (Pierce, 1/1000 dilution) or rabbit anti-human SC (Rindisbacher et al. J Biol Chem 1995; 270:14220-8; 1/500 dilution), followed by Extravidin-HRP (Sigma, 1/4000 dilution) or goat anti-rabbit-HRP (Sigma, 1/4000 dilution).

Preparation of Immune Complexes

For administration to ligated intestinal loop, $2 \times 10^6$ St or St-GFP were mixed with 100 µg of SIgASal4 or human plasma-derived pIgA, SIgA, IgM, SIgM, IgA/M, SCIgA/M or IgG, or with 20 µg of SC in 100 µl PBS. For oral infection, $2 \times 10^7$ bacteria were mixed with 200 µg, 1 mg or 5 mg of human plasma-derived IgAM or SCIgA/M in 150 µl PBS. The mixtures were incubated for 1 hour at room temperature on a rotating wheel, and subsequently used as such.

Observation by Laser Scanning Confocal Microscopy of Immune Complexes

Immune complexes formed by St-GFP and plasma-derived Abs were laid onto glass slides (Thermo Scientific), mounted with anti-fading Vectashield reagent (Vector Laboratories), and visualized immediately using a Leica SP5 confocal microscope equipped with a 63×objective. Images were processed with Imaris 8 software. To evaluate agglutination efficiency, the number of free St-GFP, the number of bacteria aggregates and their estimated size were determined on 10 different fields, in 5 independent experiments.

Mice

Four week-old female Balb/c mice were obtained from Charles River Laboratories (L'Arbresle, France) and used at the age of 7-8 weeks. They were housed in the animal facility of the Lausanne University State Hospital under standard conditions. All experiments were approved by the State Veterinary Office.

Ligated Intestinal Loops

Intestinal ligated loops were performed according to the procedure of Rey et al. (Rey et al. J Immunol 2004; 172:3026-33) with minor modifications: 100 µl of a solution containing $2 \times 10^6$ St in a free form or as immune complexes were delivered into the lumen of an intestinal ligated loop containing a PP. Mice were sacrificed 1.5 hour later, the PP was removed from the intestinal tissue, and incubated 30 min in DMEM containing 2% FCS and 100 µg/ml gentamycin to kill extracellular bacteria. A PP upstream of the ligated loop was collected to serve as noninfected control. The bacterial load was determined as described (Pigny et al. J Infect Dis 2016; 214:438-46).

Preparation of Tissue Sections and Observation by Laser Scanning Confocal Microscopy Intestinal segments containing a PP were immediately fixed in 500 µl of PBS-4% paraformaldehyde (Fluka) for 2 hours at 4° C., and further processed as described (Kadaoui K A, Corthésy B. J Immunol 2007; 179:7751-7), with minor modifications: Bacteria were detected upon incubation in PBS-5% FCS-0.1% saponin with biotinylated IgASal4 (1/50), followed by Cy5-labeled streptavidin (1/500; Amersham Biosciences). After washing, cell nuclei were stained with DAPI. Laser scanning confocal microscopy images were obtained using a Leica SP5 in multi-track mode. Raw images were analyzed and processed with Imaris 8 software. All the images presented in the paper are representative of at least 4 sections were obtained from 3D reconstructions generated from the same sections.

Ab Degradation Assay

In vitro: intestinal washes were prepared form BALB/c mice (4-6 weeks old) as described (Crottet and Corthésy (1998) J. Immunol. 161:5445-5453). 300 ng of SCIgA/M, IgA/M and IgG were mixed with 2.5 µl of intestinal washes in a final volume of 20 µl of PBS and incubated for the indicated times at 37° C. Addition of 2.5 µl of Complete™ protease inhibitor (Roche Applied Science) stopped the reaction and the degradation products were stored at −20° C. Detection of the reduced form of the heavy chain of each Ab mixture was performed by immunoblotting using goat anti-human alpha chain (1/1000; Cappel), followed by HRP-labeled rabbit anti-goat Ab (1/4000; Sigma-Aldrich) or biotinylated anti-human mu chain (1/1000; KPL) or biotinylated anti-human gamma chain (1/1000; Sigma-Aldrich) sera, followed by Extravidin-HRP (1/4000; Sigma-Aldrich).

In vivo: 2 µg unlabeled Abs were injected in a final volume of 20 µl of PBS in a mouse ligated intestinal loop. After 6 hours, mice were sacrificed, the loop's tissue and luminal content were collected and the tissue was further cut into small pieces. The samples were incubated in 50 mM HCl and Complete™ protease inhibitor (Roche Applied Science) for 16 hours at 4° C. under gentle agitation, then centrifuged for 10 minutes at 2'350×g. The clear supernatant was collected and stored at −20° C. prior to use. SDS-PAGE and immunoblot analyses were performed as for the in vitro assay.

Oral Infection of Mice and Bacterial Load Determination

Mice were orally infected with $2 \times 10^7$ St alone or complexed with plasma-derived Abs using a round tip stainless steel needle. Infected BALB/c were sacrificed 6 days post-infection and bacterial loads in PPs, MLNs and spleen were determined as described (Pigny et al. J Infect Dis 2016; 214:438-46).

Oral Infection of Mice and Passive Administration of Ab

Mice were orally infected with $2 \times 10^7$ (prophylactic and therapeutic settings) or $2 \times 10^6$ (survival in therapeutic setting) St using a round tip stainless steel needle (Pigny et al. (2016) J. Infect. Dis. 214:438-446). Mice infected with the lowest dose exhibited the expected reduced bacterial load in all tissues tested, and died at the latest on day 11 as compared to days 6-7 with a $2 \times 10^7$ dose. In the prophylactic setting, 10 mg of polyreactive SCIgA/M, IgA/M or IgG were orally administered 24 hours and 8 hours prior to bacteria infection. In the therapeutic setting, 10 mg of SCIgA/M were orally administered 1 hour or 8 hours post-infection. Bacterial loads in PPs, MLNs, spleen and liver were assessed as described (Pigny et al. (2016) J. Infect. Dis. 214:438-446). Weight of mice and disease score (Acred et al. (1994) Laboratory Animals 28:13-18) based on fur ruffling, activity, posture, eye/nose discharge and aspect of feces were recorded on a daily basis.

Assessment of Inflammation

Six days post-infection, mice were sacrificed, 4-6 PPs were collected per mouse and processed to cell suspensions (Mikulic et al. Cell Mol Immunol 2016). Cells ($1.5 \times 10^6$) were labeled with anti-CD16/32 mAbs, followed by anti-CD45, -CD3, -CD19, -CD11b, -CD11c, -Ly-6C, -Ly-6G, -F4/80 and DAPI. Frequency of neutrophils (DAPI$^-$CD45$^+$CD3$^-$CD19$^-$autofluorescence$^-$CD11b$^+$CD11c$^-$Ly-6C$^-$F4/80$^-$Ly-6G$^+$) and macrophages (DAPI$^-$CD45$^+$CD3$^-$CD19$^-$autofluorescence$^+$CD11b$^+$CD11c$^-$Ly-6C$^-$F4/80$^+$Ly-6G$^-$) were recorded with a Gallios flow cytometer (Beckman Coulter). Alternatively, $1 \times 10^6$ cells were seeded in wells of round bottom 96-well culture plates and incubated for 24 hours at 37° C.; LPS (100 ng/ml) was added in control wells. TNF-α and IL-6 secreted in the culture supernatants were quantified by ELISA (ELISA Max kits, BioLegend).

Histological Analysis of Intestinal Tissues

At sacrifice, 1-cm sections of duodenum and jejunum were collected, fixed in paraformaldehyde and cut into 5 parts before embedding in paraffin. 7-µm sections were then prepared and stained with hematoxylin and eosin to assess tissue integrity. At least 10 tissue sections per animal were observed with an Axio Imager Z1 microscope (Zeiss).

Statistical Analysis

Statistical analysis was performed using Prism software (GraphPad Software, Inc., La Jolla, Calif.). Bars represent median of each experimental group. The unpaired, non-parametric Mann-Whitney test was used to compare two experimental groups. The unpaired, non-parametric Kruskal-Wallis test, corrected with Dunn's test for multiple comparisons, was applied to compare experimental groups. ns, non-significant; *, $p<0.05$; , $p<0.01$; *, $p<0.001$; ****, $p<0.0001$.

Example 1: Plasma-Derived Antibodies Interact with St

We first tested the ability of different molecular forms of plasma-derived IgA and IgM, or IgG, or recombinant SC to interact with St by ELISA. All Abs preparations displayed a dose-dependent recognition of the bacteria, yet at different levels (FIG. 1A). The binding capacity of mIgA to St was lower than that of pIgA or SIgA, consistent with increased avidity of the latter two. Similarly, both IgM and SIgM demonstrated a potent capacity to interact with the bacteria, whereas IgA/M and SCIgA/M preparations, that contain both monomeric and polymeric Abs, showed an intermediate recognition pattern. Somewhat surprisingly, the strongest signal was obtained with IgG, suggesting a substantial St-specific humoral response in the plasma of donors (Liang L et al PloS One 2013; 8:e61838; Pulickal A S et al Clin Vaccine Immunol 2009, 16:1413-9). Consistent with a similar binding capacity of non-secretory (polymeric) and secretory forms of IgA, IgM and IgA/M, SC demonstrated a very limited ability to interact with St (FIG. 1B). When immune complexes were prepared in solution by mixing St-GFP with plasma-derived Abs, important bacterial agglutination was observed in particular with IgA/M and SCIgA/M, as shown in FIG. 2, with contribution of both IgA and IgM in the complex (Data not shown).

The agglutination capacity was quantitated by counting free (i.e. not contained in aggregates) St-GFP as compared to immune complexes prepared at different Ab/SC to bacteria ratios (5, 1, 0.2 or 0.04 µg Ab and 1 or 0.2 µg SC per $2 \times 10^4$ bacteria). About 200 free St-GFP were counted by observation field in the absence of Abs (FIG. 3). A small number of huge bacterial aggregates, containing more than 100 bacteria, were observed when immune complexes were prepared with IgA/M or SCIgA/M at a ratio of 5 or 1 µg Ab per $2 \times 10^4$ bacteria, resulting in only 20% of free St-GFP as compared to the control condition. The efficiency of agglutination diminished in the presence of 0.2 µg IgA/M or SCIgA/M, as reflected by the smaller size of formed aggregates. At a ratio of 0.04 µg Ab per $2 \times 10^4$ bacteria, complexes were barely observed. In the presence of IgG, only small bacteria aggregates were detected and at least 5 times more Ab were necessary to end up with the same number of free St-GFP when compared to IgA/M or SCIgA/M (FIG. 3). No complexes were found when SC was mixed with St.

These data demonstrate that the interaction of (S)IgA and (S)IgM with St translates into the formation of bacterial aggregates, an essential prerequisite for the prevention of pathogen entry into mucosal tissues.

Example 2: Plasma-Derived IgA/M and SCIgA/M Preparations Limit St Entry into PPs To test whether IgA/M and SCIgA/M can indeed mediate immune exclusion and prevent St entry into PPs, we administered immune complexes formed at a ratio of 1 µg Ab per $2 \times 10^4$ bacteria into ligated intestinal loops containing one PP. We first determined that the St-specific SIgASal4 mAb protecting mice when given as bag-back (Michetti et al. Infect Immun 1992; 60:1786-92) was able to significantly reduce the number of bacteria in PPs in this experimental context (FIG. 4, left). In line with their ability to mediate St agglutination, a significant decrease in bacterial load was observed in PPs after injection of immune complexes formed with IgA/M and SCIgA/M, as compared to St alone (FIG. 4). No protective effect of either IgG or SC was detected. When IgA and IgM purified from IgA/M preparation and reconstituted in secretory-like Abs were tested, both demonstrated the ability to reduce bacterial load in PPs, with superior performance of SIgM (FIG. 4). This may be explained either by the decameric valency of IgM, or the presence of some mIgA Abs in the pIgA preparation, which most likely did not participate in the protection. In addition, reduced numbers of St-GFP were observed within the follicular-associated epithelium and at the interface with the subepitehlial dome region overlying the PPs (data not shown). The sum of the data validates plasma-derived SCIgA/M and IgA/M in their function of limiting mucosal entry of St, and demonstrates the maintenance of stable immune complexes essential to ensure protective immune exclusion.

Example 3: Plasma-Derived SCIgA/M Limits St Infection and Dissemination after Oral Administration After having demonstrated that IgA/M and SCIgA/M Abs bound to St limit its diffusion from the lumen into PPs, it turned out highly relevant to evaluate whether biological activity was preserved after oral administration. An infective dose of $2 \times 10^7$ St was defined in trial experiments to ensure a reliable bacterial load in PPs and MLNs at 2 days post-oral administration, together with an associated local and systemic infection after 6 days. When combined with IgA/M and SCIgA/M at a ratio of 1 µg Ab per $2 \times 10^4$ bacteria, the number of St recovered from PPs and MLNs 2 days post-infection were significantly reduced as compared to the administration of the bacteria alone (FIG. 5A). When the infection was left to develop for 6 days, analysis of mice post-infection revealed that SCIgA/M protected mice better than IgA/M, especially with respect to dissemination beyond PPs. Increasing the ratio of Ab to 5 µg per $2 \times 10^4$ bacteria did not improve the performance of SCIgA/M, which displayed the same protective effect when the bacterial load was measured in PPs, MLNs and the spleen (FIG. 5B). In contrast, IgA/M turned out to be effective in reducing the bacterial load in PPs only. Despite a loss in statistical significance, bringing down the amount of SCIgA/M to 0.2 µg in the immune complex still allowed to lower bacterial dissemination.

Example 4: Plasma-Derived SCIgA/M Quenches Inflammatory Circuits Induced by St Infection SIgA has been demonstrated to dampen inflammatory processes in the GI tract (Mikulic J. et al (2016) Cell Mol Immunol, Mantis N et al (2011) Mucosal Immunol. 4:603-611), which is considered beneficial for the host by preventing tissue destruction in pathological situations. After oral infection with St, rapid GI inflammation is triggered; relevant markers include an increase in frequencies of neutrophils and macrophages, as well as elevated production of TNF-α and IL-6 (FIGS. 6A and B; compare uninfected with "No Ab" experimental conditions). When SCIgA/M-based immune complexes were administered, a reduction in both phagocyte recruitment and pro-inflammatory cytokine production were measured in PPs at day 6 (FIGS. 6A and B). The effect was less pronounced in presence of IgA/M. The data suggest that keeping St away from the GI epithelium ensures protection in a context which does not need to rely on exacerbated inflammatory responses (Dolowschiak et al. Cell Host Microbe 2016; 20:238-49).

Example 5: Polyreactive (SC)Ig/AM are Stable in the Gut Rnvironment

Once in the intestine, SIgA/M, but not IgA/M and IgG, is anchored to the epithelium through strong interaction with mucus (data not shown). The stability in the intestinal environment of the same set of Abs was examined by testing their susceptibility to degradation by mouse intestinal washes (See Materials and Methods). After 2 hours of incubation in intestinal washes, immunoblots performed in reducing conditions indicated the presence of intact alpha chain (62 kDa) and some degradation products (FIG. 7A).

After overnight incubation, more intact alpha chain signals were recovered for SCIgA/M preparations as compared to IgA/M, consistent with the protective role ensured by SC (Crottet and Corthésy (1998) J. Immunol. 161:5445-5453). The lesser sensitivity of mu chain to proteases in intestinal washes (Longet et al. (2014) J. Biol. Chem. 289:21617-21626) imposed to prolong digestion for up to 48 hours; the presence of SC in SCIgA/M reduced the conversion of the mu chain into degraded species (FIG. 7A). In contrast, when IgG was analyzed, the gamma chain was already largely degraded after as few as 2 hours, and almost no signal could be detected after 16 hours. Experiments performed in vivo in ligated intestinal loops showed that the degradation of alpha and mu chains from SCIgA/M and IgA/M was very partial, whereas analysis of IgG resulted in the appearance of an intense signal well below the expected molecular weight of native gamma chain (FIG. 7B). Due to the digestion time limited to 6 hours for in vivo experiments (see Materials and Methods), the presence of SC in SCIgA/M led to a limited advantage in stability as compared to IgA/M.

Together, these data demonstrate that after administration in the intestinal environment, the SCIgA/M preparation, as compared to IgA/M and IgG, combines the most optimal anchoring and stability properties, two parameters that have been associated with protective efficacy in the gut.

Example 6: Protection Against *Salmonella* Infection is Best Mediated by Prophylactic Oral Administration of SCIgA/M To test the biological activity of SCIgA/M, as well as the importance of SC in the preparation, prophylactic oral administration of 10 mg of SCIgA/M, IgA/M and IgG (as control) was performed at 24 hours and 8 hours before intragastric inoculation with $2 \times 10^7$ CFU of St. Mice were kept for 6 days post-infection, and the protective efficacy of the Abs was assessed by measuring the local intestinal and systemic bacterial load. Prophylactic passive immunization with SCIgA/M turned out to be the more potent at reducing the bacterial load in PPs, MLNs, and spleen of infected mice, and displayed similar characteristics than IgA/M when the liver was examined (FIG. 8A). Physiological symptoms of infection including weight loss and disease score were best reduced upon SCIgA/M administration (FIG. 8B). IgA/M showed some efficacy, as reflected by a significantly weaker disease score in comparison with untreated-infected mice. For all parameters assessed, prophylactic treatment with IgG yielded no sign of improvement of the health status of the animals at day 6 after infection (FIG. 8B).

St infection and its associated inflammatory response are known to damage the intestinal epithelium, leading to additional alteration of the gut function. Consistent with its capacity to limit infection, prophylactic administration of SCIgA/M, and to a lesser extent IgA/M, contributed to largely maintain the architecture of the intestinal tissue post-infection. As depicted in FIG. 8C, histological analysis of intestinal tissue showed preserved integrity of the epithelium, with only limited shortening of the villi. In comparison, untreated-infected or IgG treated-infected mice exhibited important tissue damages with destruction of the intestinal villus structure (FIG. 8C).

Example 7: SCIgA/M Delays Disease Progression and Improves Survival of Infected Mice The strict correlation between the residual bacterial load and a possible effect on the survival of prophylactically treated animal is important to validate protection in the physiological context timewise. To address this issue, the experimental focus was put on animals having received prophylactically the best protective candidate Ab as defined above, i.e. SCIgA/M at a dose of 10 mg given orally 24 hours and 8 hours prior to infection with $2 \times 10^7$ St. In contrast to control animals rapidly losing weight and reaching high disease scores (FIGS. 9A and B), 5 out of 7 prophylactically treated-infected mice showed a delay in symptom progression. When looking at the survival rate, all untreated mice died within 9 days post-infection (FIG. 9C), while 3 out of 7 survived after having received a two-dose of SCIgA/M. Overall, prophylactic passive administration of the SCIgA/M preparation has the ability to protect mice from subsequent oral infection by lethal doses of St via multiple modes of action including reduction of the bacterial load in tissues, maintenance of the epithelium architecture, and delay of disease progression or complete healing.

Example 8: Protection Against *Salmonella* Infection is Best Mediated by Therapeutic Oral Administration of SCIgA/M The promising results obtained with the prophylactic administration of polyreactive SCIgA/M prompted us to assess the therapeutic protective efficacy of this Ab preparation. When $2 \times 10^7$ St were used to orally infect mice, administration of 10 mg SCIgA/M 1 hour later was able to significantly reduce the bacterial load recovered at day 6 post-infection from both intestinal (PPs and MLNs) and systemic (spleen and liver) tissues (FIG. 10A). In parallel, weight loss and disease score of treated mice were less pronounced as compared to untreated animals (FIG. 10B). However, oral treatment performed 8 hours post-infection did not result in a reduction of the infection most likely due to the huge amount of bacteria that is lethal for all infected mice within 6-7 days. We thus sought to assess the protective efficacy of therapeutically applied SCIgA/M with 10-fold less St, a dose that remains lethal at day 11 (see FIG. 11A). Initial oral infection with $2 \times 10^6$ St followed by oral delivery of 10 mg SCIgA/M 1 h later reduced the amount of St found in either local or systemic compartments (FIG. 10C). Strikingly, delaying the time of SCIgA/M administration to 8 hours post-infection kept diminishing the bacterial load significantly. This translated into improved condition of the treated mice as compared to control animals, as demonstrated by a less massive weight loss and low disease score (FIG. 10D); however, and somehow expectedly, such protective function was more limited when compared to SCIgA/M given shortly, i.e. 1 hour after St infection.

The protective efficacy of a single dose of SCIgA/M observed 6 days post-infection led us to hypothesize that therapeutic application of these polyreactive Abs may have a positive effect on the survival of mice post-infection. We therefore orally infected mice with $2 \times 10^6$ St, and applied 10 mg of SCIgA/M 8 h later; the weight, the disease score and the survival of animals were recorded for 20 days. In the untreated control group, mice rapidly lost weight (FIG. 11A) and demonstrated signs of disease (FIG. 11B), leading to the death of all mice at day 11 post-infection (FIG. 11C). In contrast, 4 out of 8 animals therapeutically treated with one oral administration of 10 mg SCIgAM remained healthy for up to 20 days after infection, without losing weight or exhibiting signs of disease more pronounced than fur ruffling (FIG. 11C). The other half died from the infection, but displayed a delay in both weight loss and the disease score's evolution, as compared to control mice, hence leading to prolonged survival.

Altogether, our data demonstrate that a single oral therapeutic administration of polyreactive SCIgAM at a time when St infection is already ongoing entails the reduction of the intestinal and systemic bacterial load and of the symptoms associated with infection. This results in increasing the overall survival rate of infected mice to 50%, comparing with 100% mortality in the absence of therapeutic SCIgA/M.

The invention claimed is:

1. A method for promoting agglutination of *Salmonella* bacteria in the gut of a subject, comprising administering a composition comprising polyreactive secretory IgA and/or polyreactive secretory IgM to the gut of the subject, wherein the composition is not milk or obtained from milk.

2. The method of claim 1, wherein the agglutination leads to immune exclusion of *Salmonella* bacteria.

3. The method of claim 1, wherein the entry of *Salmonella* bacteria into Peyer's patches and the diffusion into mesenteric lymph nodes is inhibited.

4. The method of claim 1, wherein the composition reduces mucosal infection by *Salmonella* bacteria.

5. The method of claim 1, wherein the composition reduces local inflammation.

6. The method of claim 1, wherein the composition reduces systemic dissemination of the *Salmonella* bacteria.

7. The method of claim 6, wherein the *Salmonella* is a *Salmonella enterica* subsps.

8. A method for promoting agglutination of *Salmonella* bacteria in the gut of a subject, comprising administering a composition comprising secretory IgA and/or secretory IgM to the gut of the subject, wherein the composition is not milk or obtained from milk, wherein the secretory IgA and/or secretory IgM of the composition comprises secretory IgA and/or secretory IgM with binding specificity for *Salmonella* bacteria.

9. The method of claim 1, wherein the secretory IgA and/or secretory IgM is/are prepared by combining plasma-derived IgA and/or IgM with secretory component in vitro.

10. The method of claim 9, wherein the secretory component is recombinant secretory component.

11. The method of claim 10, wherein the recombinant secretory component is obtained by expression in a mammalian cell line.

12. The method of claim 10, wherein the secretory component is human secretory component.

13. The method of claim 1, wherein at least 10% of the protein comprised in the composition is secretory IgA.

14. The method of claim 13, wherein at least 10% of the protein comprised in the composition is secretory IgM.

15. The method of claim 13, wherein at least 10% of the protein in the composition is secretory IgA and 10% of the protein is secretory IgM.

16. The method of claim 7, wherein the *Salmonella enterica* subsps is *Salmonella Typhi*.

17. The method of claim 13, wherein at least 20% of the protein comprised in the composition is secretory IgA.

18. The method of claim 14, wherein at least 20% of the protein comprised in the composition is secretory IgM.

* * * * *

SEQUENCE LISTING

```
<160> NUMBER OF SEQ ID NOS: 1

<210> SEQ ID NO 1
<211> LENGTH: 764
<212> TYPE: PRT
<213> ORGANISM: Homo sapiens

<400> SEQUENCE: 1

Met Leu Leu Phe Val Leu Thr Cys Leu Leu Ala Val Phe Pro Ala Ile
1               5                   10                  15

Ser Thr Lys Ser Pro Ile Phe Gly Pro Glu Glu Val Asn Ser Val Glu
            20                  25                  30

Gly Asn Ser Val Ser Ile Thr Cys Tyr Tyr Pro Pro Thr Ser Val Asn
        35                  40                  45

Arg His Thr Arg Lys Tyr Trp Cys Arg Gln Gly Ala Arg Gly Gly Cys
    50                  55                  60

Ile Thr Leu Ile Ser Ser Glu Gly Tyr Val Ser Ser Lys Tyr Ala Gly
65                  70                  75                  80

Arg Ala Asn Leu Thr Asn Phe Pro Glu Asn Gly Thr Phe Val Val Asn
            85                  90                  95

Ile Ala Gln Leu Ser Gln Asp Asp Ser Gly Arg Tyr Lys Cys Gly Leu
            100                 105                 110

Gly Ile Asn Ser Arg Gly Leu Ser Phe Asp Val Ser Leu Glu Val Ser
        115                 120                 125

Gln Gly Pro Gly Leu Leu Asn Asp Thr Lys Val Tyr Thr Val Asp Leu
    130                 135                 140

Gly Arg Thr Val Thr Ile Asn Cys Pro Phe Lys Thr Glu Asn Ala Gln
145                 150                 155                 160

Lys Arg Lys Ser Leu Tyr Lys Gln Ile Gly Leu Tyr Pro Val Leu Val
                165                 170                 175

Ile Asp Ser Ser Gly Tyr Val Asn Pro Asn Tyr Thr Gly Arg Ile Arg
            180                 185                 190

Leu Asp Ile Gln Gly Thr Gly Gln Leu Leu Phe Ser Val Val Ile Asn
        195                 200                 205

Gln Leu Arg Leu Ser Asp Ala Gly Gln Tyr Leu Cys Gln Ala Gly Asp
    210                 215                 220

Asp Ser Asn Ser Asn Lys Lys Asn Ala Asp Leu Gln Val Leu Lys Pro
225                 230                 235                 240

Glu Pro Glu Leu Val Tyr Glu Asp Leu Arg Gly Ser Val Thr Phe His
                245                 250                 255

Cys Ala Leu Gly Pro Glu Val Ala Asn Val Ala Lys Phe Leu Cys Arg
            260                 265                 270

Gln Ser Ser Gly Glu Asn Cys Asp Val Val Val Asn Thr Leu Gly Lys
        275                 280                 285

Arg Ala Pro Ala Phe Glu Gly Arg Ile Leu Leu Asn Pro Gln Asp Lys
    290                 295                 300

Asp Gly Ser Phe Ser Val Val Ile Thr Gly Leu Arg Lys Glu Asp Ala
305                 310                 315                 320

Gly Arg Tyr Leu Cys Gly Ala His Ser Asp Gly Gln Leu Gln Glu Gly
```

```
                    325                 330                 335
        Ser Pro Ile Gln Ala Trp Gln Leu Phe Val Asn Glu Glu Ser Thr Ile
                        340                 345                 350
        Pro Arg Ser Pro Thr Val Val Lys Gly Val Ala Gly Ser Val Ala
                        355                 360                 365
        Val Leu Cys Pro Tyr Asn Arg Lys Glu Ser Lys Ser Ile Lys Tyr Trp
                370                 375                 380
        Cys Leu Trp Glu Gly Ala Gln Asn Gly Arg Cys Pro Leu Leu Val Asp
        385                 390                 395                 400
        Ser Glu Gly Trp Val Lys Ala Gln Tyr Glu Gly Arg Leu Ser Leu Leu
                        405                 410                 415
        Glu Glu Pro Gly Asn Gly Thr Phe Thr Val Ile Leu Asn Gln Leu Thr
                        420                 425                 430
        Ser Arg Asp Ala Gly Phe Tyr Trp Cys Leu Thr Asn Gly Asp Thr Leu
                        435                 440                 445
        Trp Arg Thr Thr Val Glu Ile Lys Ile Ile Glu Gly Glu Pro Asn Leu
                450                 455                 460
        Lys Val Pro Gly Asn Val Thr Ala Val Leu Gly Glu Thr Leu Lys Val
        465                 470                 475                 480
        Pro Cys His Phe Pro Cys Lys Phe Ser Ser Tyr Glu Lys Tyr Trp Cys
                        485                 490                 495
        Lys Trp Asn Asn Thr Gly Cys Gln Ala Leu Pro Ser Gln Asp Glu Gly
                        500                 505                 510
        Pro Ser Lys Ala Phe Val Asn Cys Asp Glu Asn Ser Arg Leu Val Ser
                        515                 520                 525
        Leu Thr Leu Asn Leu Val Thr Arg Ala Asp Glu Gly Trp Tyr Trp Cys
                530                 535                 540
        Gly Val Lys Gln Gly His Phe Tyr Gly Glu Thr Ala Ala Val Tyr Val
        545                 550                 555                 560
        Ala Val Glu Glu Arg Lys Ala Ala Gly Ser Arg Asp Val Ser Leu Ala
                        565                 570                 575
        Lys Ala Asp Ala Ala Pro Asp Glu Lys Val Leu Asp Ser Gly Phe Arg
                        580                 585                 590
        Glu Ile Glu Asn Lys Ala Ile Gln Asp Pro Arg Leu Phe Ala Glu Glu
                        595                 600                 605
        Lys Ala Val Ala Asp Thr Arg Asp Gln Ala Asp Gly Ser Arg Ala Ser
                610                 615                 620
        Val Asp Ser Gly Ser Ser Glu Glu Gln Gly Gly Ser Ser Arg Ala Leu
        625                 630                 635                 640
        Val Ser Thr Leu Val Pro Leu Gly Leu Val Leu Ala Val Gly Ala Val
                        645                 650                 655
        Ala Val Gly Val Ala Arg Ala Arg His Arg Lys Asn Val Asp Arg Val
                        660                 665                 670
        Ser Ile Arg Ser Tyr Arg Thr Asp Ile Ser Met Ser Asp Phe Glu Asn
                        675                 680                 685
        Ser Arg Glu Phe Gly Ala Asn Asp Asn Met Gly Ala Ser Ser Ile Thr
                        690                 695                 700
        Gln Glu Thr Ser Leu Gly Gly Lys Glu Glu Phe Val Ala Thr Thr Glu
        705                 710                 715                 720
        Ser Thr Thr Glu Thr Lys Glu Pro Lys Lys Ala Lys Arg Ser Ser Lys
                        725                 730                 735
        Glu Glu Ala Glu Met Ala Tyr Lys Asp Phe Leu Leu Gln Ser Ser Thr
                        740                 745                 750
```

```
Val Ala Ala Glu Ala Gln Asp Gly Pro Gln Glu Ala
    755                 760
```